(12) United States Patent
Diel et al.

(10) Patent No.: US 11,952,566 B2
(45) Date of Patent: Apr. 9, 2024

(54) OVERPRESSURE PROTECTION MEANS

(71) Applicant: Sartorius Stedim Biotech GmbH, Göttingen (DE)

(72) Inventors: Bernhard Diel, Dransfeld (DE); Andreas Klemm, Kassel (DE); Matthias Hielscher, Hessisch Lichtenau (DE); Alexandre Espachs, Göttingen (DE); André Grebe, Malsfeld (DE)

(73) Assignee: Sartorius Stedim Biotech GmbH, Göttingen (DE)

( * ) Notice: Subject to any disclaimer, the term of this patent is extended or adjusted under 35 U.S.C. 154(b) by 741 days.

(21) Appl. No.: 17/052,942

(22) PCT Filed: Jan. 4, 2019

(86) PCT No.: PCT/EP2019/050128
§ 371 (c)(1),
(2) Date: Nov. 4, 2020

(87) PCT Pub. No.: WO2019/211006
PCT Pub. Date: Nov. 7, 2019

(65) Prior Publication Data
US 2021/0238533 A1    Aug. 5, 2021

(30) Foreign Application Priority Data
May 4, 2018   (DE) .................. 10 2018 003 676.7

(51) Int. Cl.
*C12M 3/00*      (2006.01)
*C12M 1/00*      (2006.01)
(Continued)

(52) U.S. Cl.
CPC ............ *C12M 41/40* (2013.01); *C12M 23/28* (2013.01); *C12M 23/40* (2013.01); *C12M 23/58* (2013.01); *C12M 41/48* (2013.01)

(58) Field of Classification Search
CPC ...... C12M 23/28; C12M 41/40; C12M 23/40; C12M 23/58
See application file for complete search history.

(56) References Cited

U.S. PATENT DOCUMENTS

2011/0207170 A1     8/2011  Niazi
2013/0295662 A1*   11/2013  Cadwell ............... C12M 21/00
                                                    435/317.1
(Continued)

FOREIGN PATENT DOCUMENTS

DE    11200402636 T5    12/2006
DE    102016101350 B3    2/2017
(Continued)

OTHER PUBLICATIONS

International Search Report issued in International Application No. PCT/EP2019/050128 dated Apr. 16, 2019.

*Primary Examiner* — Nathan A Bowers
(74) *Attorney, Agent, or Firm* — Quinn IP Law

(57) ABSTRACT

The invention relates to an apparatus 10 for storing and/or processing at least one medium 11, in particular a bioprocessing device, comprising at least one disposable container 1, which is designed to accommodate at least some of the at least one medium 11, and at least one overpressure protection means 5, which is fluid-connected to the at least one disposable container 1. The at least one overpressure protection means is designed, when triggered, to conduct at least some of the at least one medium 11 into an apparatus region 3a' in front of the overpressure protection means 5 in relation to a flow direction F, in particular into the at least (Continued)

one disposable container 1 and/or into at least one further, second container 1*a*.

9 Claims, 10 Drawing Sheets

(51) Int. Cl.
*C12M 1/34* (2006.01)
*C12M 1/36* (2006.01)

(56) References Cited

U.S. PATENT DOCUMENTS

| | | | | |
|---|---|---|---|---|
| 2014/0377739 | A1* | 12/2014 | Welch | C12M 47/02 |
| | | | | 435/286.5 |
| 2016/0145555 | A1* | 5/2016 | Ingber | C12M 29/20 |
| | | | | 435/29 |
| 2016/0298810 | A1* | 10/2016 | Maggiore | C12M 23/28 |
| 2017/0233268 | A1* | 8/2017 | Carucci | C02F 1/5227 |
| | | | | 210/705 |

FOREIGN PATENT DOCUMENTS

| | | | |
|---|---|---|---|
| EP | 3078735 | A1 | 10/2016 |
| WO | 2014044612 | A1 | 3/2014 |

* cited by examiner

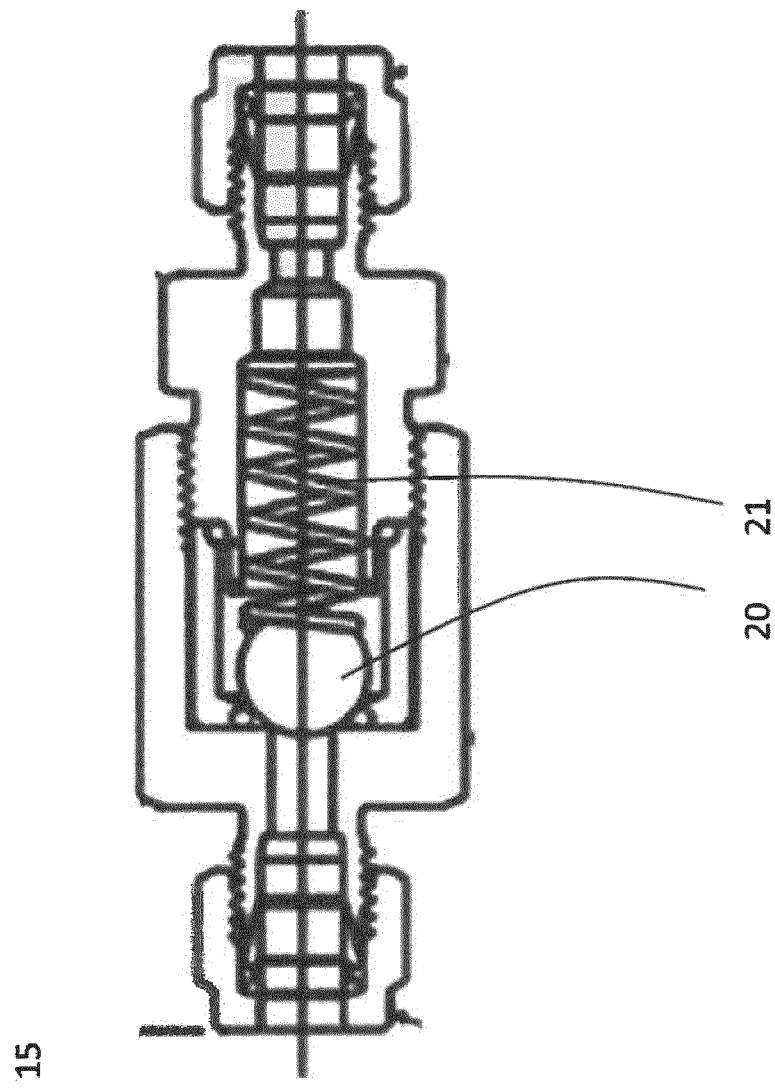

OVERPRESSURE PROTECTION MEANS

The application relates to a method, a device comprising a disposable container and an overpressure protection means and a system which is provided with the device for storing and/or treating and/or processing and/or preparing at least one medium, and for at least partially collecting the at least one medium when the overpressure protection means is activated.

The disposable container may in particular be a "single-use bag". A disposable container is substantially a container which is generally disposed of after it has been used, in particular after it has been used once. In specific cases, a disposable container may also be configured to be used several times, in particular, two, three or four times, but it is not configured for permanent use. A single-use container may, for example, be formed from a plastics material, in particular from a deformable synthetic material. In particular, the mentioned disposable containers are configured or suitable for being used as components of bioprocess installations. The use of such disposable containers in biomethod technology is particularly advantageous compared with conventional high-grade steel containers with regard to costs and the flexibility thereof.

Furthermore, a disposable container and generally a disposable system can preferably be sterilized substantially easily. In particular, a disposable container is already in a sterilized state prior to use so that the user does not have to take any measures in this regard. This enables the user to reduce the risk of contamination with harmful substances, in particular as a result of the single use and the subsequent disposal since cleaning and/or preparation of the disposable container, which involves a risk of contamination, can be prevented.

However, a decisive factor in the consideration between the use of a disposable container and a steel container is the reliability of the operations. In the case of overpressure, with a disposable container a fracture and/or a crack and/or a leakage in the container, in particular in the container wall thereof, can occur comparatively easily. Consequently, there may be a leakage of the container, a loss of a medium and a contamination of the environment by the medium and/or the medium by the environment. The contamination may consequently relate, on the one hand, to the environment which may become contaminated with the material which has leaked and/or been discharged. In particular the medium may be and/or contain a biologically dangerous substance as a result of the uncontrolled escape of which into the environment users may be exposed to dangerous substances. The contamination may, however, on the other hand, also relate to the leaked and/or discharged medium which may become contaminated by substances from the environment.

If a medium, in particular a fluid medium, such as a gas and/or a liquid and/or a granulate and/or a powder, is directed and/or introduced into a system and/or a container, an increasing pressure may be produced particularly if the filling is not correctly regulated and/or the system and/or the container is/are not accordingly ventilated. The pressure of the medium can lead to the container exceeding the maximum pressure or the bursting pressure of the device and/or the container and/or the system. The maximum pressure or the bursting pressure is the pressure from which a portion of the system and/or the device and/or the container, for example, forms a leak and at least a portion of the medium can be discharged from the system and/or the device and/or the container.

A so-called overpressure application and/or an uncontrolled exceeding of a maximum pressure or maximum permissible pressure and/or a bursting pressure may, for example, causally precede malfunctions of a primary ventilation filter. An overpressure application may, for example, be brought about as a result of clogging with a condensate, by jamming or closure of the primary ventilation filter, by an incorrectly input value and/or a faulty controller and/or a closed valve and/or a hose clamp or a hose line which is closed in another manner. Furthermore, a pump speed may be adjusted to be excessively high and/or some other inputs relating to correct control, monitoring and/or ventilation may be incorrectly adjusted so that a pressure which increases in an uncontrolled manner may be produced. An uncontrolled overpressure may consequently bring about leakages in the hose material used, in connection pieces and/or in or on components of the device or even cause them to burst. Sensors which are installed in the device may also be impaired and in particular destroyed.

Generally, with disposable systems or single-use systems (SU systems) and/or disposable containers, the pressure is monitored and/or controlled and/or regulated by means of pressure sensors and control units. The pressure is accordingly indirectly controlled. In the event of a malfunction of a control unit and/or incorrect installation and/or a malfunction of the pressure sensor which is configured to measure and monitor the operating pressure. malfunctions may accordingly occur. Furthermore, an incorrect signal may be transmitted to the control which can also lead to the maximum permissible operating pressure being exceeded in an uncontrolled manner.

The maximum permissible pressure of a device and/or a container and/or a system which is also referred to as bursting pressure in the context of this application corresponds to the value of the maximum pressure which a device can withstand without overpressure protection means and from which when exceeded the device at least partially or at least at one portion bursts and/or splits and/or breaks and/or forms a leak.

The activation pressure of an overpressure protection means is the value of the maximum pressure which an overpressure protection means withstands and from which, when exceeded, the overpressure protection means is activated or activates. The activation pressure is preferably substantially lower than the maximum permissible pressure at the location at which the overpressure protection means is arranged and/or installed and/or integrated in the device. The activation pressure should, however, not be a great deal lower than the maximum permissible pressure.

The object of the present invention is accordingly to provide a device with a disposable container for at least partially storing and/or processing at least one medium with improved reliability.

This object is achieved by the independent claims. The aspects of subject-matter of the dependent claims represent preferred embodiments.

The invention relates to a device for storing and/or treating and/or processing and/or preparing at least one medium, in particular a bioprocess device, comprising at least one disposable container, in particular a disposable bag of a bioreactor, which is configured to at least partially receive at least one medium and the volume of which is preferably configured to at least partially store and/or treat and/or process the at least one medium; and at least one overpressure protection means which is connected to the at least one disposable container in fluid terms, wherein the at least one overpressure protection means is configured, in the event of an activation or the activation thereof, to guide the at least one medium at least partially or at least a portion of at least one of the at least one medium into a device region which is arranged upstream of the overpressure protection means with respect to a flow direction, in particular into the at least one disposable container; and/or into at least one additional second container, wherein the flow direction relates in particular to a flow and/or material flow of at least a portion of the at least one medium and can preferably be produced by means of a pressure-producing means.

In other words, a device comprises one or more disposable containers and one or more overpressure protection means. The at least one disposable container is connected to the at least one overpressure protection means in fluid terms. For example, the disposable container and the overpressure protection means may be components of a single system which is closed, in particular hermetically closed (or separated from an environment in fluid terms). The two spatial regions in which the two components are located can then communicate with each other with respect to the pressure and/or in fluid terms. For example, a pressure may be equalized between two spatial regions. The overpressure protection means may be activated in particular by exceeding a specific (predetermined or predeterminable) activation pressure. That is to say that the pressure in the device and in particular directly at the overpressure protection means exceeds a pressure which is greater than the specific activation pressure and the maximum possible pressure which an overpressure protection means withstands. After the overpressure protection means has been activated, at least a portion of the at least one medium, in particular the portion of the at least one medium which passes through the activated overpressure protection means, is discharged and/or returned to a collection container in each case and/or into a device region which is arranged upstream of the overpressure protection means with respect to a flow direction, in particular into the at least one disposable container. A device region which is arranged upstream of the overpressure protection means with respect to a flow direction may, for example, be part of a line through which the at least one medium passes or can pass before it passes through the activated overpressure protection means. The activated overpressure protection means forms in particular one or more opening(s) and/or the activated overpressure protection means becomes permeable for at least a portion of the at least one medium. That is to say, a bursting disk which is also known as a single-use membrane can burst and form an opening and/or a membrane may become permeable when an activation pressure is exceeded.

The single-use container and the overpressure protection means do not, however, necessarily have to form a closed system with each other. They can also form a substantially open system which is at least partially open in the direction toward the environment. A permanent and durable open connection between two spatial regions in which the disposable container and the overpressure protection means are located and which can communicate with each other with regard to the pressure is also not absolutely necessary under any circumstances. The spatial regions may also sometimes be substantially shielded or separated from each other by a barrier, for example, a clogged filter and/or by a pump.

In particular, the device may comprise one, two, three, four, five or more disposable containers. The device may further comprise one, two, three, four, five, six or more overpressure protection means. A device may further have or comprise one, two, three, four, five, six or more discharges and/or one, two, three, four, five, six or more bypass lines and/or be or be able to be connected to the respective discharges and/or bypass lines. The discharges and/or bypass lines can be or become connected in fluid terms by means of one and the same or by means of a plurality of overpressure protection means to one or more different regions of the device. The flow direction or the substantial flow direction of at least a portion of the at least one medium in at least a part and/or a portion of the device may, for example, be brought about by a pressure-producing means, in particular a pump and/or a heat source, and/or a mechanical press and/or a gradient and a weight force of at least a portion of the medium. The term "pressure-producing means" is also intended to explicitly refer to the inherent weight force of at least a portion of the at least one medium. Accordingly, a pressure-producing means may comprise a plurality of pressure-producing means.

The device described can prevent the uncontrolled escape of material when in single-use process solutions and/or devices with at least one disposable container an overpressure is produced, for example, by means of a pressure-producing means which is used, and in a borderline case causes or can cause leakages and/or fractures. Consequently, a loss of at least a portion of the medium can be prevented.

It is further possible to prevent a pressure within at least a portion of the device when a specific (predetermined or predeterminable) activation pressure and/or a maximum permissible pressure is exceeded at least from increasing further since at least a portion of the at least one medium is discharged and/or returned in a substantially controlled manner into a collection container and/or the disposable container. Furthermore, in particular a gas, after an overpressure protection means has been activated, may be provided with a larger volume which enables the gas to expand in order to consequently reduce the pressure or at least to limit it to a predetermined value. The operation mentioned, in particular the activation and the opening of the overpressure protection means, preferably takes place directly, in particular mechanically, that is to say, substantially without control by means of signals and/or transmission of signals, for example, electrical signals. The overpressure protection means accordingly represents at least one desired breaking location which, from an activation pressure or when an activation pressure is exceeded, forms an opening for controlled discharge of at least a portion of the medium. The overpressure protection means may, for example, be selected in accordance with a specific activation pressure. Additionally or alternatively, the overpressure protection means may be adjusted to a desired activation pressure or be selected in accordance with a desired activation pressure. In this instance, the desired activation pressure corresponds to the pressure in the device from which, when exceeded, in particular the pressure in the disposable container at least is intended not to rise further and the overpressure protection means is intended to be activated. For example, the specific activation pressure of the overpressure protection means and/or the maximum permissible pressure of the device may be able to be adjusted and can preferably be adjusted by the user as required.

In addition, a contamination of the medium with substances in the environment and/or a contamination of the environment with materials in the medium can also be prevented using the device described. For example, it is possible to prevent a material of the at least one medium, for example, a cell culture medium, from being discharged from the device in an uncontrolled manner and consequently becoming contaminated by substances in the environment. This is particularly the case when the device forms a sterile and closed system and at least a portion of the at least one medium substantially within the closed system is either returned, for example, into the disposable container and/or directed into a collection container.

The device described is further particularly advantageous when the application risk is increased, when, for example, toxic, infectious and/or aggressive substances and/or hazardous substances are contained in the at least one medium and are intended to be processed.

Furthermore, the device described may advantageously prevent high-quality and/or rare and/or valuable substances which may be contained in the at least one medium inside the device from becoming lost in the event of overpressure and the impending threat of possible bursting and/or breakage and/or explosion of a component of the device. In particular in the pharmaceutical industry, there is significant interest in minimizing risk during processing since pharmaceutical active ingredients may often be of considerable value.

Generally, a discharged fluid may be guided under pressure into a container, in particular a feed vessel, so that a process fluid which is used does not have to be discarded, but can instead be further prepared.

Using the device, a higher level of operational reliability can accordingly be achieved. In addition to conventional technical control means, such as the process control and the process assurance, for example, comprising disposable pressure sensors, the device can accordingly additionally optimize or at least improve the reliability during the treatment and/or processing and/or storage of hazardous and/or noxious and/or sensitive and/or valuable substances.

Another advantage may be that the installation of pressure sensors in some cases can be completely dispensed with so that a simplified and/or cheaper device can be provided. Furthermore, as a result, it is also possible under some circumstances to dispense with complex maintenance of such pressure sensors which can lead to a further simplification and cost reduction. In particular, the user may accordingly find the operation of the device to be uncomplicated and simplified.

According to an aspect, the at least one overpressure protection means is integrated directly in container walls of the at least one disposable container, in particular the overpressure protection means terminates in a substantially positive-locking manner with the container wall.

A particularly simple and advantageous handling is achieved if the overpressure protection means is integrated in a portion of a container wall of the disposable container, which portion is as flat as possible, so that, for example, no protruding components can disturb or can become damaged during transport and/or use.

It is additionally possible to prevent a user from having to assemble the components comprising the overpressure protection means and disposable container prior to use when these components are already connected to each other during production by the manufacturer. This may particularly be the case when a bursting disk is integrated in particular in a substantially positive-locking manner in the container wall.

According to an aspect, the at least one overpressure protection means comprises a disposable overpressure protection means, in particular a mechanical disposable overpressure protection means, which is at least partially formed from a high-grade steel and/or a plastics material.

All the advantages of the use of disposable components apply when a disposable overpressure protection means for single use is used. The term "single use" relates in the case of a disposable overpressure protection means to single activation. After a single activation, the disposable overpressure protection means can be disposed of. If the disposable overpressure protection means is substantially fixedly installed with a disposable device and/or a disposable container and/or is integrated therein, the term "single use" may also refer to the single use of the disposable device and/or the disposable container without the disposable overpressure protection means having to be activated. For example, the entire device, as long as all the components are configured for single use, can be disposed of as a whole after they have been used once. In this instance, it is possible to prevent contamination from occurring during complete or partial preparation and/or cleaning of the device. Furthermore, the use of disposable components has been found to be particularly comfortable. If substantially relatively cheap materials have been processed in the device, the disposal after a single use may also be found to be cost-effective with respect to multiple use with preparation and cleaning.

According to an aspect, the at least one overpressure protection means comprises at least one of the following, without being limited thereto: a bursting disk, an overflow valve, a safety valve, a membrane and in particular an electrical and/or mechanical force limiter of a pump.

The overpressure protection means mentioned, in particular a bursting disk, an overflow valve, a safety valve, a compression valve and/or a membrane, have been found to be particularly simple, readily sterilizable and relatively cost-effective components. The use and/or provision of these overpressure protection means require(s) no handling and/or no significant knowledge by the user. The respective technology on which the implementation of a bursting disk, an overflow valve, a safety valve, a membrane and a compression valve is based is simple and reliable. In particular, a pressure on at least one portion of the device can be limited directly by the mentioned overpressure protection means to a predetermined value. In this instance, the activation of the respective overpressure protection means is substantially mechanical and in particular completely mechanical. The term "mechanical" is intended in particular to be understood to mean that merely the pressure which exceeds a maximum value or a specific (predetermined or predeterminable) activation pressure is sufficient to activate the overpressure protection means. It is accordingly not necessary for a signal, for example, an electrical and/or optical or similar signal, to be necessarily transmitted from a sensor to the overpressure protection means in order to activate it. This embodiment therefore advantageously represents another device with increased reliability.

According to an aspect, the device further comprises at least one discharge which is configured, when the at least one overpressure protection means is activated, to direct the at least one medium at least partially into the at least one disposable container and/or into at least one second container. Preferably, the discharge is integrated and/or fitted in or on the overpressure protection means, particularly when the overpressure protection means is already integrated and/or fitted in or on the container wall. Optionally, the discharge may be constructed integrally with the overpressure protection means. The discharge may also be constructed integrally with the overpressure protection means and the container wall of the disposable container.

The discharge enables the user to discharge in a defined manner a medium which overflows or which is discharged through an activated overpressure protection means. For example, the relevant component of the at least one medium may be discharged and/or directed away into another container. If the components mentioned are formed integrally with each other, there is a particular advantage in that contact locations between the components can be prevented. Such contact locations may leak or become leaky, wherein contamination could occur from outside or inside the device. Therefore, this embodiment represents another device with increased reliability.

Furthermore, the use for the user is particularly simple and comfortable since he/she may have to use no or fewer measures for assembly. Furthermore, assembly can also be dispensed with during production, which can make the production more efficient and accordingly more cost-effective.

According to an aspect, the at least one overpressure protection means is activated by means of an electrical signal, in particular at least one sensor. In an embodiment, an overpressure protection means may be activated in a purely mechanical manner, whereas another overpressure protection means can be activated by means of an electrical signal. In addition, an overpressure protection means which can be activated mechanically can also be activated electrically.

In other words, an overpressure protection means may optionally be activated directly by exceeding an activation pressure or by means of an electrical signal, for example, of a pressure and/or temperature sensor. A pressure and/or temperature sensor may to this end send an electrical signal to the overpressure protection means and trigger the activation thereof. Additionally or alternatively, a second overpressure protection means can be activated by an electrical signal of a first overpressure protection means when the first overpressure protection means is activated. Alternatively, however, the second overpressure protection means is completely activated by means of an electrical signal, whilst the first overpressure protection means is mechanically and/or electrically activated. In addition to a first and a second overpressure protection means, additional overpressure protection means which can be activated in all conceivable variations may be provided.

If an overpressure protection means has been incorrectly produced and, for example, cannot be activated by means of the predetermined activation pressure, or if a "false" overpressure protection means which is activated from a higher activation pressure than the maximum permissible pressure has been incorrectly provided, the overpressure protection means can additionally be activated by an electrical signal, for example, transmitted by a pressure sensor in order to achieve another degree of reliability. Additionally or optionally, the signal may also be transmitted by a temperature and/or a gas or an optical sensor to the overpressure protection means. For example, in the event of reaching a predetermined or predeterminable maximum temperature of at least a portion of the medium, an electrical signal can be transmitted in order to activate the overpressure protection means so that a medium with an excessively high temperature is discharged and this portion of the medium with an excessively high temperature is substantially prevented from possibly damaging and/or impairing temperature-sensitive elements of the device and/or other media therein.

If a large number of (two, three or more) overpressure protection means are provided, it may be advantageous for, if one overpressure protection means is activated mechanically by an activation pressure being exceeded, the other overpressure protection means on which the local (partial) pressure has potentially not yet reached and in particular exceeded the respective maximum value, to be electrically activated. In this manner, it is possible to produce additional openings, through which at least a portion of the at least one medium, for example, a fluid (in particular a gas) can expand and escape in a controlled manner and/or can be discharged and/or collected in a controlled manner. In this instance, it is possible to prevent in advance a pressure from increasing in various portions of a device after the respective overpressure protection means have been activated. Consequently, the reliability of the device can be additionally improved. This embodiment accordingly represents another device with increased reliability.

According to an aspect, an overpressure protection means may send a signal to another component of the device when activated. In particular, an overpressure protection means when activated may transmit an electrical signal to a pump which causes the pump to switch off. Alternatively or additionally, an overpressure protection means when activated may transmit a signal to at least one other protection unit and cause this unit to switch off or activate a function. For example, the main protection unit of a power supply may receive via an overpressure protection means when it is activated a signal which causes the power supply to be switched off by the main protection unit.

A feedback between an overpressure protection means and another element, for example, another protection unit and/or a motor and/or a pump, has the advantage that at least parts of the system can be completely switched off in the event of danger when an overpressure protection means has been activated once. This may prevent other components of the at least one medium from being discharged and/or escaping through the open overpressure protection means and a collection container potentially overflowing as a result. In particular, it is also possible to prevent a further increase of the pressure in other portions of the device. This embodiment accordingly also represents another device with increased reliability.

The invention further relates to a system comprising:
- at least one disposable container which is configured to at least partially receive the at least one medium;
- at least one overpressure protection means which is connected to the at least one disposable container in fluid terms;
- a main line for fluid connection of the at least one disposable container to a target container; and
- at least one discharge which is configured, when the at least one overpressure protection means is activated, to direct the at least one medium at least partially into at least one additional container; and/or
- a bypass line which is configured, when the at least one overpressure protection means is activated, to direct the at least one medium at least partially back into the device region which is arranged upstream of the overpressure protection means with respect to a flow direction, in particular into a portion of the main line and/or into the at least one disposable container, wherein the at least one overpressure protection means is arranged on the discharge and/or the bypass line and, when the at least one overpressure protection means is activated, the discharge and/or the bypass line is/are connected in fluid terms to the main line.

In other words, it is a system comprising one of the above-mentioned devices, in particular according to a preferred embodiment, wherein the system further comprises:

a main line for fluid connection of the at least one disposable container to an additional third container which corresponds to a target container or is a target container; and at least one discharge which is configured, when the at least one overpressure protection means is activated, to direct the at least one medium at least partially into the at least one additional second container; and/or a bypass line which is configured, when the at least one overpressure protection means is activated, to direct the at least one medium at least partially back into the device region which is arranged upstream of the overpressure protection means with respect to the flow direction, in particular a portion of the main line and/or into the at least one disposable container, wherein the at least one overpressure protection means is arranged on the discharge and/or the bypass line and, when the at least one overpressure protection means is activated, the discharge and/or the bypass line is/are connected in fluid terms to the main line.

In particular, portions of the system or volumes of the system, in particular containers and/or lines and/or discharges and/or bypass lines after the activation of an overpressure protection means form physical communicating pipes which can exchange a fluid and a pressure if a fluid connection exists between the corresponding components or portions.

In addition to the advantages of the embodiments of a device, the system described has further advantages which involve its entirety but also the individual components thereof. The provision of a main line enables the user to spatially separate a portion of the medium which has been subjected to a process and/or an operation from the portion of the medium which has not yet been subjected to this process and/or operation.

The provision of a discharge and/or a bypass line has the advantage that a medium which after an overpressure protection means has been activated passes through the means, can be discharged in a defined and controlled manner and/or returned into a region which is located upstream of the overpressure protection means with respect to a flow direction. A defined and/or controlled discharge or return of at least a portion of the medium involves the path which the medium takes between the overpressure protection means and the target volume. For example, the medium may be directed at least partially through a hose and/or a pipe. Furthermore, it is possible to define and/or control whether the part-system in which and/or through which at least a portion of the medium is guided is intended to represent a substantially closed or a substantially open system. Furthermore, all the physical parameters, such as volume, pressure, temperature, etcetera, can be defined and/or controlled.

The provision of a discharge and/or a bypass line may have the advantage that, depending on requirements, a suitable target volume can be selected. For example, the target volume for a portion of the medium which is discharged by means of a discharge may involve a collection container. The target volume can, for a portion of the medium which is returned by means of a bypass line, involve the region which is arranged upstream of the overpressure protection means with respect to a flow direction, in particular the disposable container.

According to an aspect, the system comprises the additional third container which is configured to at least partially receive the at least one medium and which is preferably a disposable container.

An advantage of providing another container in addition to the disposable container and where applicable to a collection container is that a medium which is located at least partially in the disposable container can be transferred to the additional container if, for example, a chemical and/or biological process has been carried out in the disposable container. For example, the medium on its path to the other container may pass through a filter, where it is at least partially cleaned and/or filtered before it reaches the other container. In this manner, a portion of the medium which has been subjected to a process and/or an operation can be spatially separated from the portion of the medium which has not yet been subjected to this process and/or operation.

The provision of another disposable container has the advantage that another component of the system can be disposed of after single use. The advantages of the provision of disposable containers have already been set out above.

According to an aspect, the system comprises at least one pressure-producing means, in particular a pump, wherein the at least one pressure-producing means is configured to pump at least a portion of the at least one medium from the at least one disposable container into the third container in the flow direction.

The provision of a pressure-producing means enables the user to convey at least a portion of the at least one medium into another region of the system and/or device, for example, into an additional container, via a main line. In particular, the pressure-producing means may produce a material flow or a flow of a portion of the at least one medium and/or a pressure drop.

A pressure-producing means may in particular be at least one pump. The at least one pump may in particular comprise a hose pump, membrane pump, centrifugal pump and/or a peristaltic pump. Any other known pump for producing a pressure drop and/or a material stream or flow is further conceivable. Preferably, a pressure-producing means comprises at least one from: a single-use or disposable valve, optionally with a spring, a single-use check valve or disposable non-return valve or non-return valve for single use, a bursting disk with an "internal loop" or at least partially integrated bypass and/or discharge, a bursting disk with an "external loop" or non-integrated external bypass and/or discharge.

A similar pressure-producing means may also be a mechanical press or piston and/or another means which compress a flexible disposable container, for example, by mechanical pressing pressure by means of activation and/or by means of weight force.

A pressure-producing means may also comprise a gradient or an arrangement with a gradient and/or a carrier or technical equipment and/or device which produces a gradient with respect to the gravitational direction. For example, the disposable container which is at least partially filled with a medium can be connected in fluid terms to another container and positioned in a slightly raised state with respect thereto so that the weight force of the medium itself ensures that there is a pressure which produces a material flow or a flow of at least a portion of the medium from the disposable container to the other container.

A pressure-producing means may also comprise a heat source which, as a result of the action on at least a portion of the at least one medium, ensures the expansion thereof or even the change thereof from the aggregation state, for example, from a liquid to a gas. The expansion thereof produces, as long as the container substantially retains its volume, a pressure which may also be in the position to produce a material stream or a flow of at least a portion of the medium from the disposable container to the other container.

According to an aspect, the at least one pressure-producing means, in particular a pump, is arranged on the main line and is configured to produce a pressure drop along the main line.

The provision of a pump on the main line has the advantage that, for example, a portion of the at least one medium from a portion of the system which is arranged upstream of the pump with respect to the flow direction can be drawn into the main line. The portion of the at least one medium which passes through the pump can subsequently be conveyed and/or pumped into a portion of the system which is arranged downstream of the pump, for example, through a filter into another container.

According to an aspect, the at least one pressure-producing means is arranged on the disposable container and is configured to produce a pressure drop within the disposable container and/or along the main line.

The mentioned embodiment has the advantage that a disposable container can be filled with the application of pressure and therefore the operation of filling can be accelerated.

According to an aspect, the discharge and/or the bypass line and in particular the overpressure protection means is/are arranged with respect to the flow direction downstream of the pressure-producing means and/or on a main line. Alternatively or additionally, the at least one overpressure protection means may be arranged on a different component of the device and/or the system from the disposable container and/or the main line, for example, on a third container.

The mentioned arrangement of the discharge and/or the bypass line directly downstream of or behind the pressure-producing means with respect to a flow or path direction has the advantage that at least a portion of the medium can be discharged and/or returned when the overpressure protection means is activated. This may, for example, be activated by an excessively high pump power and/or by means of a blockage in a filter and/or in the main line. In particular, an overpressure protection means is arranged on the discharge and/or the bypass line.

According to an aspect, the system further comprises a feedback, in particular an electrical feedback, preferably between the overpressure protection means and pressure-producing means, wherein the feedback is configured to switch off the pressure-producing means when the at least one overpressure protection means is activated. In other words, the said overpressure protection means preferably has a feedback which can transmit a signal, preferably an electrical signal, to the pump after the activation, wherein the signal causes the pump to switch off and the pump power to be adjusted. This embodiment has the advantage of providing a particularly reliable system.

According to an aspect, the discharge and/or the bypass line and in particular the overpressure protection means is/are integrated at least partially in the pressure-producing means.

The above-mentioned embodiment has the advantage that components can be processed or integrated in each other, which can make the use particularly simple. Furthermore, in this manner, subsequent assembly by the user can be prevented so that particularly comfortable use is enabled.

According to an aspect, at least the disposable container and/or the overpressure protection means can be sterilized, in particular is/are at least partially constructed from a plastics material and/or a high-grade steel. In other words, the disposable container and/or the overpressure protection means and/or the entire device and/or the system is/are at least partially configured to be able to be sterilized using a validated method, preferably using at least one from gamma irradiation, autoclaving, vapor sterilization and chemical sterilization means.

A sterilizable element has the advantage that it can come into contact with media, for example, cell cultures which, for example, are not intended to be contaminated with biological substances. It is further advantageous for components or elements of a device, in particular disposable components, to be sterilized already upon purchase or ex works and to be sold in a sterilized state so that the user does not have to take any measures for sterilization before he/she places the device and/or system into operation.

According to an aspect, the overpressure protection means further comprises a valve for equalizing pressure relationships or for draining or reducing a pressure by means of material flow in a predetermined or predeterminable direction. Furthermore, the overpressure protection means may comprise a return flow prevention device for preventing a return flow of a medium which has already been discharged by an overpressure protection means.

According to an aspect, the overpressure protection means has an activation pressure which corresponds to a value of the maximum pressure which the overpressure protection means tolerates or withstands or the overpressure protection means resists at a maximum and from which, when exceeded, the overpressure protection means is activated. The activation pressure is preferably adjusted and/or selected in such a manner that it is substantially lower than the maximum permissible pressure or the bursting pressure of the container and/or the device and/or the system, in particular at the location at which the overpressure protection means is arranged on the device.

If the activation pressure has a value which is lower than the maximum permissible value or the bursting pressure of the container, under normal circumstances bursting and/or breaking and/or cracking and/or damage of the container and/or the device and/or the system can be prevented. Consequently, it is also possible to prevent a portion of the medium from being discharged in an uncontrolled manner from the container and/or the device and/or the system and instead it can be discharged in a controlled manner.

According to an aspect, the overpressure protection means comprises at least one layer and/or material and/or film or ply layer, preferably with desired breaking locations, wherein the layer and/or the material and/or the film or ply layer is/are configured in such a manner that it/they break(s) when it is/they are subjected to a pressure which exceeds the activation pressure.

According to an aspect, the overpressure protection means comprises a portion of the container wall of the disposable container, wherein the container wall at least partially comprises a film and the overpressure protection means is part of this film and has a film structure of the film layer which is weakened in at least one position or which has a desired breaking location in order to adjust the activation pressure or in order to be activated when the activation pressure is exceeded. Preferably, the film structure and in particular the desired breaking location are produced by means of expansion, perforation, chemical processing and/or physical processing. In particular, the overpressure protection means according to this embodiment is formed integrally with the disposable container.

There is an advantage to constructing the overpressure protection means as a component of the film since material and/or complexity and/or costs can be saved in this manner. The above-mentioned embodiment enables a particularly simple or straightforward and/or cost-effective solution with increased reliability.

According to an aspect, the at least one overpressure protection means, in particular the bursting disk and/or the film layer is/are configured with a desired breaking location to break in a fragment-free manner when it is/they are activated.

A fragment-free bursting of an overpressure protection means may prevent splinters and/or fragments and/or small particles and components of the overpressure protection means from reaching the medium and/or the device and/or the system and/or the pump. Consequently, it is possible to avoid and/or prevent them from having to be prepared and/or cleaned and/or freed of the fragments after bursting, which can be linked with a high level of complexity.

According to an aspect, the device further comprises at least one sensor which is configured to indicate when the overpressure protection means has been activated and in particular the desired breaking location is broken after the activation pressure has been exceeded.

A sensor which can indicate whether the overpressure protection means has been activated may, for example, also be configured to transmit a signal to another element of the device and/or the system in order to switch off an element, for example, a pump and/or an operation. Therefore, this particular embodiment has increased reliability for the user.

According to an aspect, the overpressure protection means, in particular the bursting disk and/or the film layer having a desired breaking location, comprises at least one membrane and/or a membrane filter, wherein the membrane and/or the membrane filter is/are configured to have an activation pressure which substantially corresponds to the maximum permissible or bursting pressure. Consequently, for example, only one component of the at least one medium can be discharged via the overpressure protection means whilst other components of the medium remain in the system and/or in the device. For example, a medium may comprise a solid and a liquid, for example, suspended solid particles which are present in a liquid. If the activation pressure of the membrane and/or the membrane filter is exceeded, the liquid can escape and be discharged, whilst the solid material or the solids remain in the system and/or the device. This is particularly advantageous when the material which is intended to remain in the system and/or the device is particularly sensitive with respect to, for example, fluctuations (for example, temperature, pressure, atmosphere, etcetera).

According to an aspect, a bursting disk may be installed and/or arranged and/or fitted by means of a tri-clamp connection in or on the disposable container and/or the device and/or the system. According to another aspect, at least one discharge and/or at least one bypass line and/or at least one main line may comprise and/or constitute a "plastics material pipe" device.

Tri-clamp connections can be used universally and can be provided as substantially cost-effective connections.

The invention further relates to a method for at least partially collecting at least one medium in a device, comprising the steps of:
    providing at least one disposable container which is configured to at least partially receive the at least one medium;
    providing at least one overpressure protection means which is connected to the at least one disposable container in fluid terms; and,
    in the event that the overpressure protection means is activated:
        discharging the at least one medium at least partially into an additional second container by means of a discharge; and/or
        returning the at least one medium at least partially into a device region which is arranged upstream of the overpressure protection means with respect to a flow direction, in particular into the at least one disposable container, by means of a bypass line.

Specific embodiments of the method may further have features of the above-mentioned embodiments of a device and/or a system. A method can accordingly have the above-mentioned advantages of the individual features.

The invention is explained in greater detail below with reference to embodiments which are shown in Figures. Individual features which are shown in the Figures can be combined with other embodiments as long as they are not mutually exclusive. The same reference numerals refer in this instance to components of the embodiments which are identical or similar. In the drawings:

FIG. 10 shows a non-return valve according to an embodiment.

Figure 1:
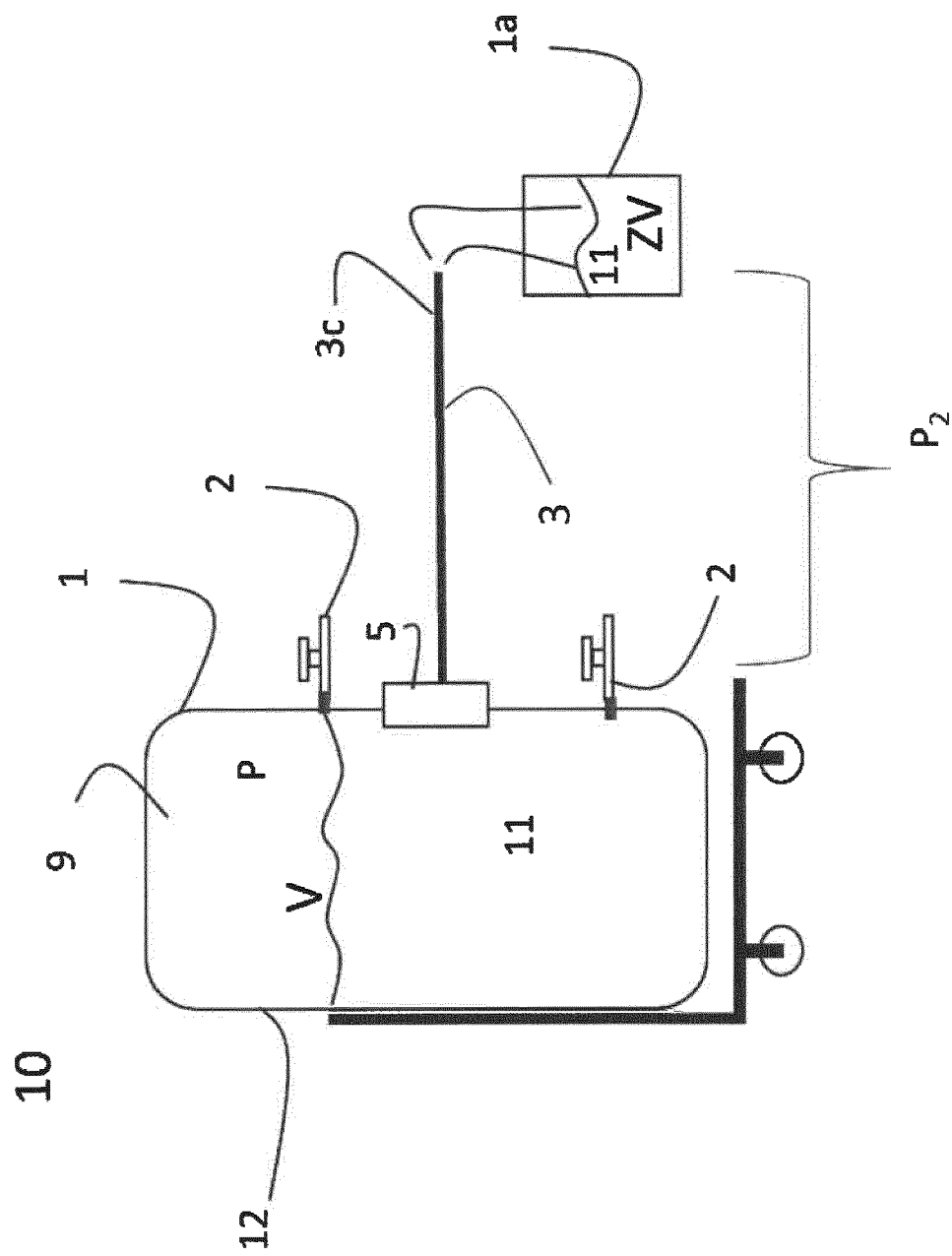
FIG. 1 is a schematic side view of a cross-section of a device comprising a disposable container, an overpressure protection means and a discharge according to an embodiment.

FIG. 1 shows a device 10 according to an embodiment comprising at least one disposable container 1 having a volume V and at least one overpressure protection means 5. The overpressure protection means 5 is arranged on the container wall 12 of the disposable container 1 and in particular integrated therein. Furthermore, the disposable container 1 comprises two inlets and/or outlets 2, through which a medium can be introduced into and/or discharged from the disposable container 1. In an embodiment which is not shown here, a disposable container 1 comprises more than two inlets and/or outlets 2 or only one inlet and/or outlet. In other words, the disposable container 1 can be filled with the medium via the inlets and/or outlets 2 and/or (at least partially) emptied via them. In this instance, the medium may be or comprise a fluid (in particular a liquid and/or gas) and/or a solid material.

In the disposable container 1 there is in particular at least one fluid medium 11 and a gas which is located above. In the disposable container 1 there is applied a mean pressure P which may comprise partial pressures but which preferably substantially do not differ from each other substantially powerfully (for example, by no more than approximately 10%, preferably no more than approximately 1%). The disposable container 1 forms with the overpressure protection means 5 a system 9 which is substantially closed or hermetically closed or separated from an environment as long as the overpressure protection means 5 has not been activated. The overpressure protection means 5 may in particular comprise a bursting disk and/or a membrane and/or a membrane filter. Alternatively or additionally, the overpressure protection means 5 may represent a portion of the container wall 12 which has a structuring, in particular a desired breaking location.

As soon as the pressure P in the closed system exceeds a specific (predetermined or predeterminable) activation pressure of the overpressure protection means 5, the overpressure protection means 5 opens and/or bursts or breaks so that the closed system becomes an open system, in particular with a connection relating to the pressure with respect to the outer side. At least a portion of the at least one medium can pass through the overpressure protection means 5 and be introduced along a line 3, which in this instance corresponds to a discharge 3c and which comprises a pipe, into at least one target volume ZV of another second container 1a, in particular a collection container. In the embodiment shown, the path which the at least one portion of the medium 11 takes through the discharge 3c to the collection container 1a is not a closed system. Since the level of the medium within the disposable container 1 extends below the height of the lower of the two inlets and/or outlets 2, a gas can also escape.

A disposable container 1 is a container which is configured for single use. After the disposable container 1 has been used once, it has generally performed its function and can be disposed of. For example, a disposable container 1 is produced from plastics material which may comprise polyamide, polycarbonate, polyethylene, polystyrene, polyethersulfone, polypropylene, polytetrafluoroethylene, polyvinyl chloride, cellulose acetate and/or ethyl vinyl acetate, but is not limited thereto. In an example, the disposable container 1 may be substantially rigid, that is to say, its form cannot be modified. In another example, the disposable container 1 may have (at least partially) flexible walls or flexible container walls 12, that is to say, the disposable container 1 can change its shape without breaking.

Disposable containers 1 may be used, for example, for critical applications in particular in the biopharmaceutical and bioproduction industry. The use of one of the disposable containers 1 may include the following, but without being limited thereto: storing a medium (for example, product), mixing and/or cell cultivation. The disposable container 1 is in particular a sterilizable disposable container 1 which is made of plastics material and which is configured to receive or hold at least one fluid.

It may be or comprise a bioreactor bag, a mixing container a 2D and/or a 3D bioprocess bag.

For example, a disposable container 1 may comprise a housing or container walls 12 with a multi-layer film structure, that is to say, a superimposition of thin sheets of plastics materials which provides a secure barrier between the contents of the disposable container 1 (for example, biohazardous material) and the external environment. Furthermore, a disposable container 1 may, for example, be provided in a pre-sterilized state (for example, by means of gamma irradiation and/or autoclaving). A disposable container 1 may consequently represent an advantageous alternative to conventional glass and/or high-grade steel systems.

The disposable container 1 may at least partially comprise at least one medium 11 which contains a fluid, for example a gas, a liquid and/or a mixture thereof, wherein the phases may be present separately and/or in a substantially "mixed" state. The pressure P in the disposable container 1 acts substantially on the walls of the housing or the container walls 12 of the disposable container 1. In one example, the housing 100 may be a Biostat® Cultibag® STR-Bioreactor bag or a Flexsafe/Flexel mixing/storage flexboy, etcetera.

The overpressure protection means 5 is connected in terms of flow medium or in fluid terms to the disposable container 1 and in particular the container walls 12 thereof by a fluid flow or a material flow from the container wall 12 to the overpressure protection means 5 being enabled. In other words, there is substantially no obstacle which cannot be overcome under normal circumstances and which impedes the medium from flowing from the container wall 12 to the overpressure protection means 5. In one example, the overpressure protection means 5 may be integrated directly in the container walls 12, for example, the container walls 12 may be fitted and/or arranged integrally in the container wall 12 without a mechanical connection piece.

The overpressure protection means 5 may, for example, be positioned and/or arranged at least partially inside a multi-layer structure of the container walls 12 (for example, a flange may be embedded and/or soldered in one or more layers of the multi-layer structure).

In another example, the overpressure protection means 5 may be connected to the container walls "externally", in particular by means of a connection piece. The overpressure protection means 5 may, for example, be arranged on an external additional container 1b and/or on a line which in each case can be connected to the container walls 12 by means of a connection, such as a hose connection.

Connection pieces and/or connections, such as lines, may preferably comprise aseptic connections, such as, for example, aseptic connectors, in particular OPTA® connectors. In an example, the overpressure protection means 5 is configured to be sterilized prior to being assembled on the disposable container 1, for example, using gamma irradiation, chemical sterilization means (such as evaporated hydrogen peroxide, ethylene oxide, etcetera), vapor sterilization and/or autoclaving. In another example, the overpressure protection means 5 can be sterilized together with the disposable container 1, in particular the container walls 12 thereof.

Figure 2:
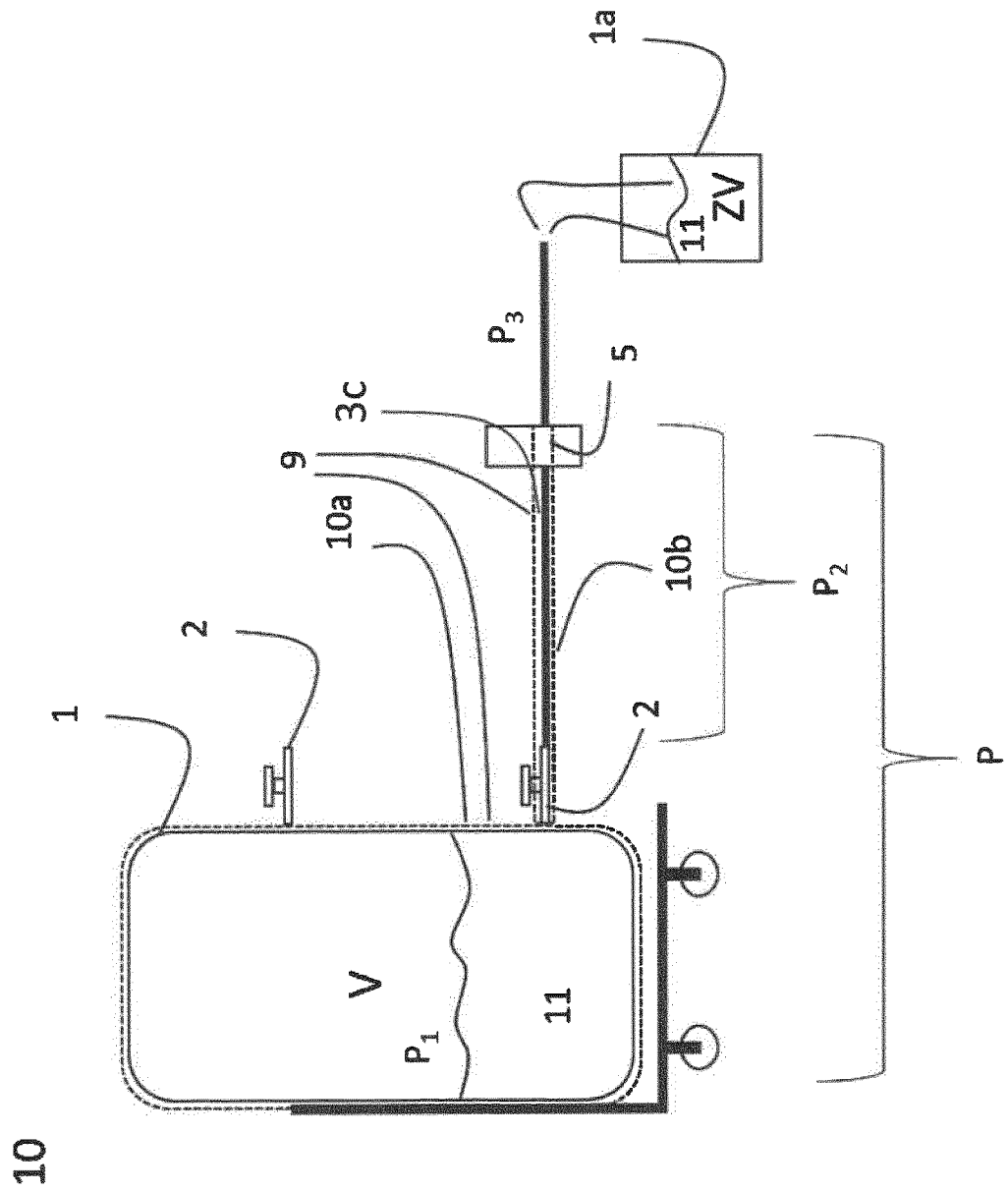
FIG. 2 is a schematic side view of a cross-section of a device comprising a disposable container, an overpressure protection means and a discharge according to another embodiment.

FIG. 2 shows a device 10 according to an embodiment comprising a disposable container 1 having a volume V and a line which corresponds to a discharge 3c on which an overpressure protection means 5 is arranged. Furthermore, the disposable container 1 comprises in particular two inlets and/or outlets 2, wherein the line is arranged or can be arranged on one of the two inlets and/or outlets 2. In the disposable container 1 is at least one fluid medium 11 and a gas above it, which can be considered to be another medium. The disposable container 1 can be considered to be a first part-system 10a, which may be open or closed, depending on whether one or both of the inlets and/or outlets 2 is/are open or closed in each case. The line may be considered to be a second part-system 10b which may be open or closed, depending on whether the inlet and/or outlet 2 on which the line is arranged is/are open or closed in each case.

As long as the inlet and/or outlet 2 on which the line is arranged is/are open, the line forms with the disposable container 1a closed system in which there is a mean overall pressure P and which is indicated with a dashed line. In the first open or closed system 10a, comprising the disposable container 1, there may be a pressure, in particular a partial pressure $P_1$. In the second open or closed system 10b comprising the line, there may be a pressure, in particular a partial pressure $P_2$. Normally, a fluid medium 11 during filling, for example, through the upper inlet and/or outlet 2, may flow into the line, where it is prevented by the overpressure protection means 5 from escaping from the line as long as the pressure P in the device, in particular the pressure $P_1$ in the line, does not exceed the activation pressure.

In the disposable container 1 there is a mean pressure P which may include partial pressures $P_1$ and $P_2$ which differ from each other, as long as the systems are connected to each other, but preferably not substantially powerfully (for example, by no more than approximately 10%, preferably no more than approximately 1%). The disposable container 1 forms with the overpressure protection means 5 a substantially closed or hermetically closed system 9 as long as the overpressure protection means 5 has not been activated.

As soon as the pressure P, in particular the partial pressure $P_2$ in the closed system exceeds the specific activation pressure of the overpressure protection means 5, the overpressure protection means 5 opens and/or bursts or breaks so that the closed system comprising the two part-systems 10a and 10b becomes an open system, in particular having a connection with respect to the pressure toward the outer side. At least a portion of the at least one medium can pass through the overpressure protection means 5 and be introduced along the line into a target volume ZV of a second container 1a. Also in this embodiment set out, the path which at least a portion of the medium 11 takes through the discharge 3c to the collection container 1a is not a closed system.

The medium 11 which is discharged can in this manner be directed in a controlled, defined and/or guided manner through the line into a collection container 1a. Consequently, it is possible to prevent the discharged medium from being lost. Furthermore, it is possible to prevent the medium from reaching and potentially contaminating the environment.

Downstream of the overpressure protection means 5 there is a pressure $P_3$ which, as long as the system is an open one, may be a local pressure of the environment. Alternatively, the system may also downstream of the overpressure protection means constitute a closed system at a controlled and/or predetermined pressure. This is particularly advantageous when the discharged medium 11 contains substances which are volatile, that is to say, readily change from a fluid state into a gaseous state and/or media and/or substances which should not come into contact with the environment. The same applies to a medium 11 which comprises a gas.

Figure 3:
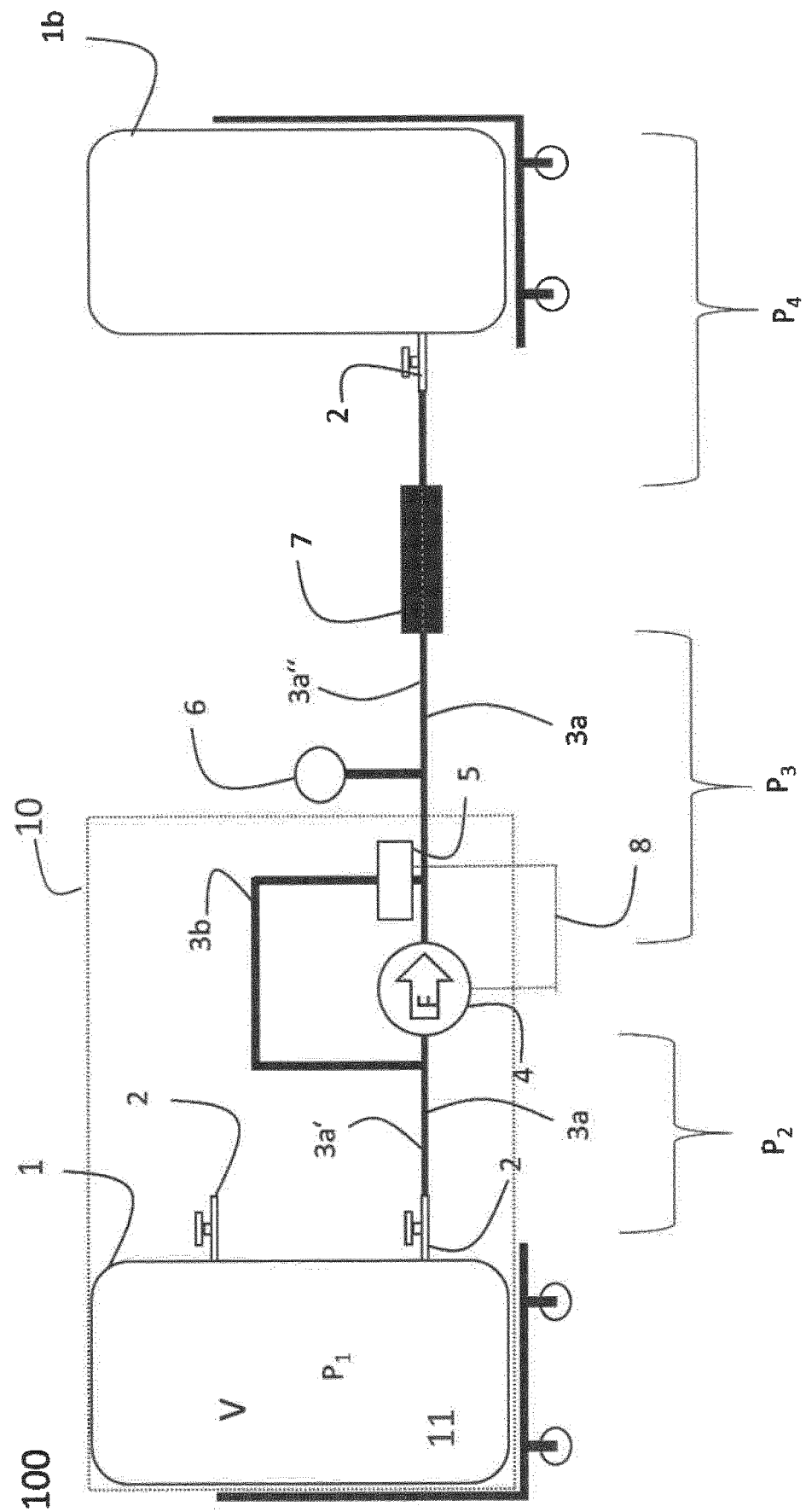
FIG. 3 is a schematic side view of a system having a device comprising a disposable container, a pump, an overpressure protection means and a bypass line according to an embodiment.

FIG. 3 shows a system 100 according to an embodiment which comprises a device 10. The device 10 comprises a disposable container 1 having a volume V which is configured to at least partially receive at least one medium 11. The disposable container 1 has two inlets and/or outlets 2 which can be opened and/or closed separately by hand and/or automatically (for example, by means of a control or regulation device which is not shown). In alternative embodiments, disposable containers comprise more than two or less than two inlets and/or outlets. At the lower inlet and/or outlet 2, there is arranged a main line 3a which is configured to guide a material flow or a stream comprising at least a portion of the at least one medium 11 in a local flow or stream direction F.

The main line 3a substantially connects the disposable container 1 to another container 1b which is also referred to as a third container 1b if it is assumed that a first container 1 corresponds to the disposable container 1 and a second container 1a corresponds to a collection container. However, the system 100 does not necessarily have to comprise a collection container 1a. At least a portion of the at least one medium 11 in the disposable container 1 can accordingly reach the third container 1b along the main line and in the flow direction F by means of a pressure-producing means 4, in particular a pump. Furthermore, the at least one medium 11 at least partially passes through a filter 7 which is arranged on the main line 3a and/or forms a portion of the main line 3a. As a result of an inlet and/or outlet 2 of the additional or third container 1b, the at least one medium 11 at least partially reaches the inner space of the additional or third container 1b. The additional or third container 1b may in particular also be another disposable container. Alternatively, the additional or third container 16 may also be or comprise a reusable container.

In the disposable container 1 there is substantially applied a mean pressure $P_1$, which is in particular homogeneous or spatially constant. In the portion of the main line 3a between the inlet and/or outlet 2 of the disposable container 1 and the pump 4 there is a pressure $P_2$. As long as the mentioned inlet and/or outlet 2 of the disposable container 1 is open, the two pressures $P_1$, $P_2$ may be substantially identical or only slightly different.

During operation of the pressure-producing means 4, in particular a pressure drop along the main line 3a is produced so that in the portion of the main line 3a between the inlet and/or outlet 2 of the disposable container 1 and the pressure-producing means 4 there is a lower pressure $P_2$ than in the portion "behind" the pressure-producing means 4 in the direction of the third container 1b. The pressure $P_3$ between the pressure-producing means 4 and the filter 7 is accordingly greater than the pressure $P_2$ which is applied with respect to the flow direction F upstream of the pressure-producing means 4. The pressure drop along the main line 3a may in particular extend in a substantially continuous manner or increase abruptly, in particular in the direct vicinity of the pressure-producing means 4. With a substantially continuous increase, the mean pressure $P_3$ would, for example, comprise different partial pressures, whereas with an abrupt increase the pressure $P_3$ in the region between the pressure-producing means 4 and filter 7 is distributed in a substantiality locally homogeneous manner.

A filter 7 substantially represents a resistance for a material stream or flow, for which reason with respect to the flow direction F "behind" the filter 7 there is applied a different pressure $P_4$ from previously. It may accordingly be the case that $P_4$ has a smaller value than $P_3$. As long as there are substantially no resistances between the filter 7 and the third container 1b and the inlet and/or outlet 2 of the third container 1b is open, the pressure $P_4$ can be distributed in a substantially locally homogeneous manner in the third region 1b and in the corresponding portion of the main line 3a.

In the above-mentioned configuration, at least a portion of the at least one medium 11, driven by a pressure-producing means 4, flows from the disposable container 1 into the third container 1b. The corresponding portion of the at least one medium 11 is in this manner filtered in the flow direction F so that potentially suspended particles from the corresponding portion of the at least one medium 11 can be filtered. Furthermore, it may the case that in the disposable container 1 at least one chemical and/or biological and/or biochemical and/or physical process takes place and a portion of the at least one medium, for example, a sediment and/or a supernatant of the sediment which have formed during the at least one process, is/are intended to be transferred into the additional container 1b. In the additional or third container 1b, the transferred portion of the at least one medium 11 can be spatially separated from the other portion of the at least one medium 11 remaining in the disposable container 1. Furthermore, the portion of the at least one medium 11 which has been transferred into the third container 1b can be further processed and/or discarded and/or stored.

The above-described case corresponds in particular to normal operation of the system 100. In rare cases, there may be malfunctions, in particular when the pressure at a location or position in the system 100 exceeds a bursting pressure of the system 100. There may occur at the corresponding location cracks and/or fractures and/or leakages, through which at least a portion of the medium 11 can be discharged. At a particularly fragile and/or critical position where there is the likelihood of a pressure exceeding a bursting pressure of the system 100 and/or the device 10, an overpressure protection means 5 may be installed to assist. FIG. 3 shows such a critical location between the pressure producing element 4 or the pump and the filter 7. In one scenario, an excessively high pump power may be adjusted at the pump 4 so that a larger volume of the medium 11 is pumped than can flow away through the main line 3a. This state results in the pressure $P_3$ between the pump 4 and filter 7 constantly rising. In another scenario, it may be the case that the filter is clogged and consequently forms a high level of resistance, as a result of which the pressure $P_3$ upstream of the filter 7 also constantly increases. Also in this instance, the pump power at the pump 4, even if it was correctly adjusted at the beginning, is so high that a larger volume of the medium 11 is pumped than can flow away or pass through the main line 3a and in particular the filter 7. If no suitable overpressure protection means 5 is installed at the corresponding location, it may be the case that the system 100 breaks or bursts at this location. Accordingly, in the system 100 of FIG. 3 an overpressure protection means 5 is arranged on the main line 3a, in particular on a side arm of the main line 3a between the pump 4 and filter 7.

As soon as the pressure $P_3$ exceeds an activation pressure of the overpressure protection means 5, the overpressure protection means 5 is activated and directs at least a portion of the at least one medium 11 into a bypass line 3b. The bypass line 3b is configured to return the corresponding medium 11 into a portion 3a' of the system 100 which is located upstream of the overpressure protection means 5—with respect to the stream or flow direction F in the main line 3a—and thus of the main line 3a. This is possible when the pressure $P_2$ in front of the pump 4 has a lower value than the pressure $P_3$ between the pump 4 and filter 7. In this manner, the pressure $P_3$ in a portion 3a'' of the system 100 located downstream of the overpressure protection means 5—with respect to the flow direction F in the main line 3a—and of the main line 3a, can be reduced or at least limited.

In a particularly advantageous manner, there is a feedback 8 between the overpressure protection means 5 and the pump 4 since the feedback 8 may be a signal which is configured to switch off the pump 4, and consequently brings about no further pressure build-up by means of the pump 4 between the pump 4 and filter 7. The feedback 8 may, for example, be an emergency switch or an emergency signal which in the event of an emergency switches off the pump 4 and/or the entire system 100, in particular all the processes which are being carried out therein. The feedback 8 may further also be and/or comprise another signal which can activate an alarm.

Furthermore, a barometer 6 which is arranged on the main line 3a between the pump 4 and the filter 7 can measure a local pressure $P_3$. This barometer 6 can be used to improve the reliability of the system 100 since a user can control the pressure $P_3$ during operation of the system 100.

Figure 4:
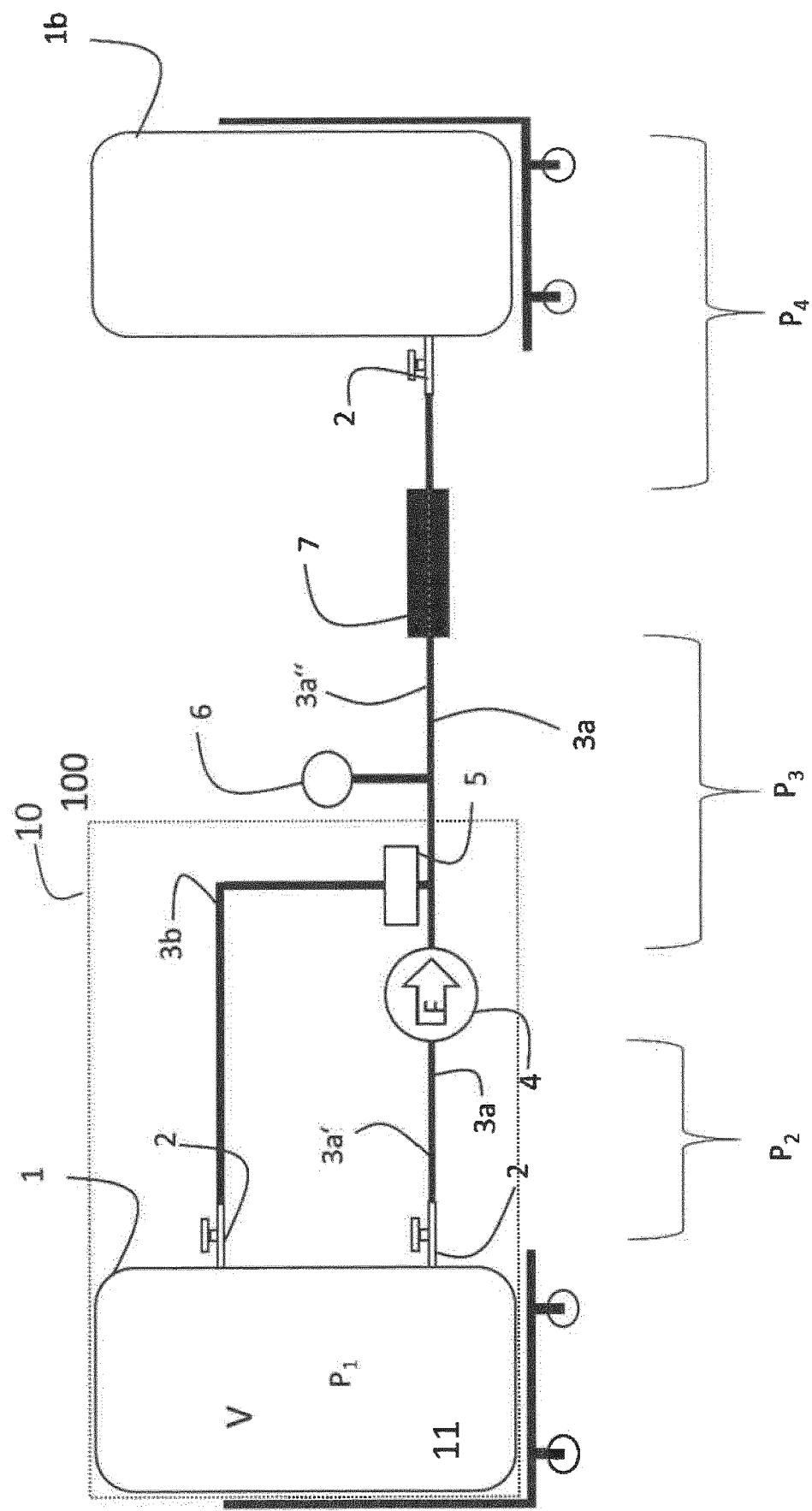
FIG. 4 is a schematic side view of a system having a device comprising a disposable container, a pump, an overpressure protection means and a bypass line according to another embodiment.

FIG. 4 also shows a system 100 according to another embodiment which comprises a device 10. In this embodiment shown, if the pressure $P_3$ exceeds an activation pressure of the overpressure protection means 5, the overpressure protection means is activated and at least a portion of the at least one medium 11 is discharged into the bypass line 3b. In this case, the bypass line 3b is configured to return the corresponding medium 11 into a portion 3a' of the system 100 located upstream of the overpressure protection means 5—with respect to the stream or flow direction F in the main line 3a—into the disposable container 1. This is possible when the pressure $P_1$ in the disposable container 1 has a lower value than the pressure $P_3$ between the pump 4 and filter 7. In this manner, the pressure $P_3$ in a portion 3a'' of the system 100 located downstream of the overpressure protection means 5—with respect to the flow direction F in the main line 3a—and thus of the main line 3a, can be reduced or at least limited.

If a feedback, as illustrated in FIG. 3, were integrated in the system 100, this could transmit a signal to the inlets and/or outlets 2, in particular the lower inlet and/or outlet 2, in order to close it/them so that no further medium 11 can be conveyed from the disposable container 1. Such a feedback may be integrated in the system 100, but this does not necessarily have to be the case. The feedback is not shown in this illustration. Furthermore, the pump 4 could optionally be switched off by means of the signal. Furthermore, a ventilation valve in the system 100 could also be caused by means of the signal to ventilate the system 100 and to equalize at least a partial pressure of the pressure P in the system 100 with respect to the ambient pressure in order to prevent another potentially uncontrolled increase of the pressure P in the system 100. Generally, the pressure P may correspond to a mean overall pressure and/or one of the partial pressures $P_1$, $P_2$, $P_3$, $P_4$.

As a result of the redirection or return of a portion of the at least one medium 11 into the disposable container 1, this portion can be saved from an uncontrolled discharge. In particular, it can be supplied again to the portion of the medium 11 which has remained in the disposable container 1.

Figure 5:
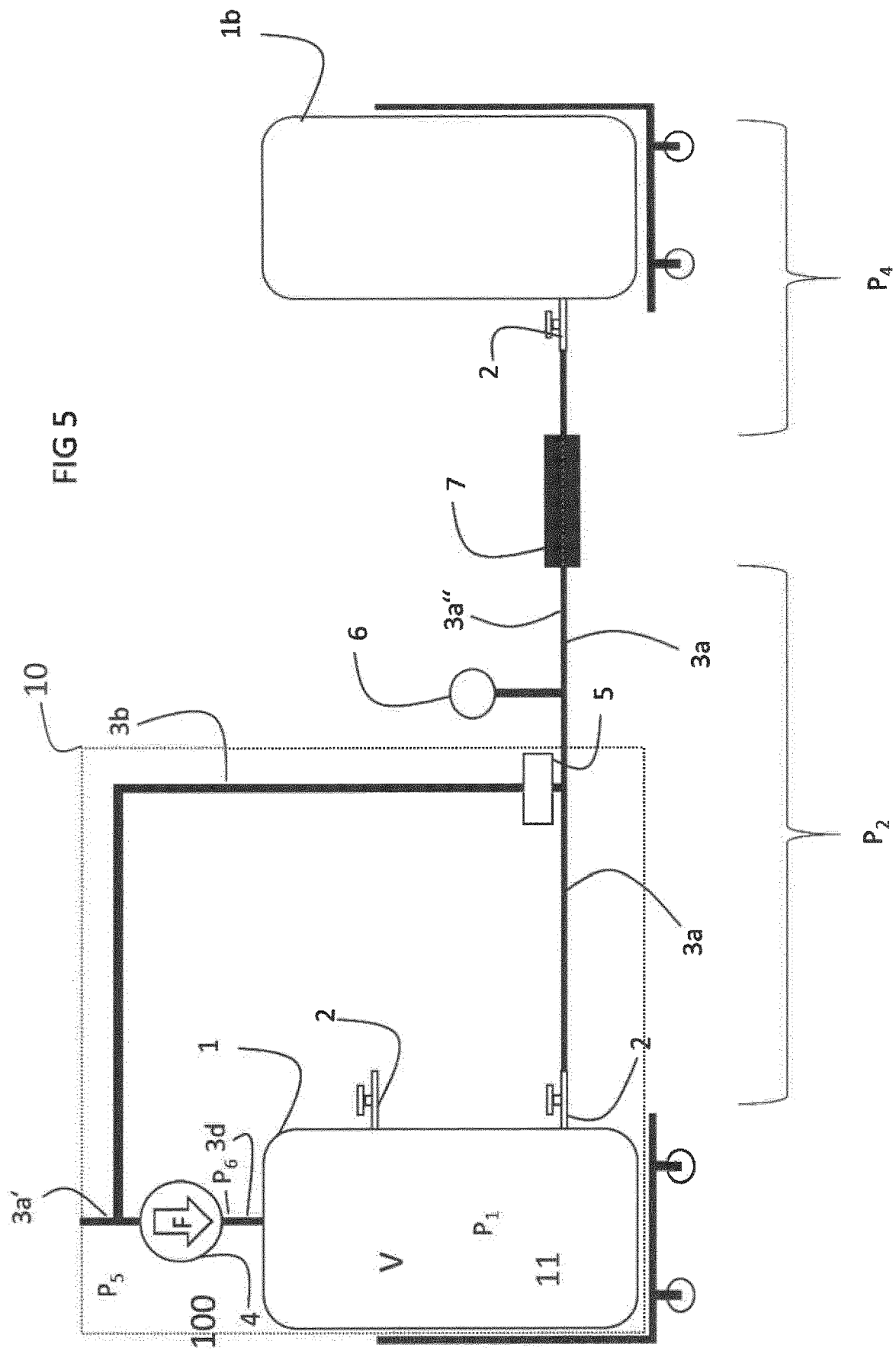
FIG. 5 is a schematic side view of a system having a device comprising a disposable container, a pressure-producing means, an overpressure protection means and a bypass line according to another embodiment.

FIG. 5 also shows a system 100 according to another embodiment which comprises a device 10. In this embodiment shown, at least one pressure-producing means 4 is arranged at a location of the system 100 at which a medium 11 can be pumped and/or conveyed and/or introduced into the disposable container 1. The disposable container 1 may accordingly be considered to be a "pressurized" container. The pressure-producing means 4 may also in this instance comprise and/or constitute a pump. It may be assumed that the disposable container 1 is connected via the main line $3a$ in fluid terms to the third container or the additional container $1b$.

The pressure-producing means 4 conveys the at least one medium 11 which is intended to be introduced into the disposable container 1 at a pressure $P_6$ into the disposable container 1 so that a pressure $P_1$ is produced and/or increases in the disposable container 1.

If the pressure $P_2$ in the main line exceeds an activation pressure of the overpressure protection means 5, the overpressure protection means 5 is activated and at least a portion of the at least one medium 11 is discharged into the bypass line $3b$. In this case, the bypass line $3b$ is configured to return the corresponding medium 11 into a portion $3a'$ of the system 100 which is located upstream of the overpressure protection means 5—with respect to the stream or flow direction F in the main line $3a$—a line which is arranged upstream of the disposable container 1. This is possible when the pressure $P_5$ in the line which is arranged upstream of the disposable container 1 has a lower value than the pressure $P_2$ between the disposable container 1 and filter 7. In this manner, the pressure $P_2$ in the main line $3a$ and/or the disposable container 1 can be reduced or at least limited. In this instance, the pressure $P_1$ in the disposable container 1 substantially corresponds to the pressure $P_2$ in the main line $3a$ as long as there is no significant resistance between the disposable container 1 and the main line $3a$.

Also in this embodiment there may be a feedback, as shown in FIG. 3, between the overpressure protection means 5 and the pressure-producing means 4, wherein the pressure-producing means 4 can be switched off by means of a signal of the feedback. Such a feedback may optionally be integrated in the system 100 shown, but this does not necessarily have to be the case. The feedback is not shown in this illustration.

The inlets and/or outlets 2 shown may be present in an open and/or in a closed state. Each inlet and/or outlet 2 may thus be either open or closed. In particular, an inlet and/or outlet 2 can be opened in order to equalize a pressure P, for example, a pressure $P_1$, in the disposable container 1 with respect to the ambient pressure and/or in order to reduce this pressure $P_1$.

Figure 6:
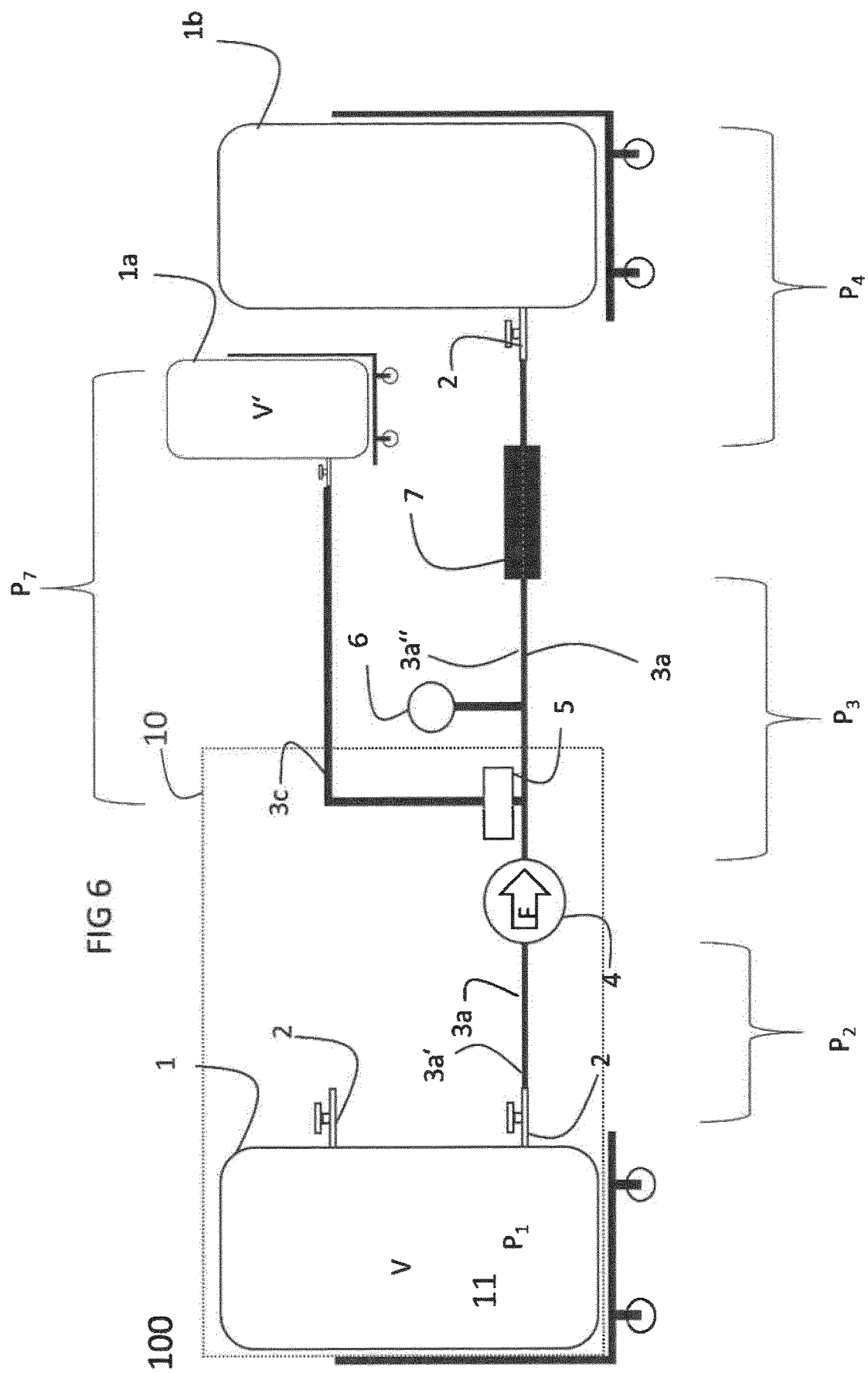
FIG. 6 is a schematic side view of a system having a device comprising a disposable container, a pump, an overpressure protection means and a discharge according to another embodiment.

FIG. 6 also shows a system 100 according to another embodiment, which comprises a device 10. The system comprises a disposable container 1, a second container $1a$ which can be understood to be a collection container and a third container $1b$ into which at least a portion of the at least one medium 11 is intended to be conveyed during normal operation, that is to say, without exceeding the activation pressure of the overpressure protection means 5.

As soon as the specific (predetermined or predeterminable) activation pressure of the overpressure protection means 5 has been exceeded in the immediate environment thereof, the overpressure protection means 5 is activated and at least a portion of the at least one medium 11 is thus supplied via the discharge $3c$ to the volume V of the second container $1a$ as long as the pressure $P_7$ in the discharge and the second container $1a$ does not exceed the activation pressure which in this instance when the overpressure protection means 5 is activated corresponds to the pressure $P_3$.

Figure 7:
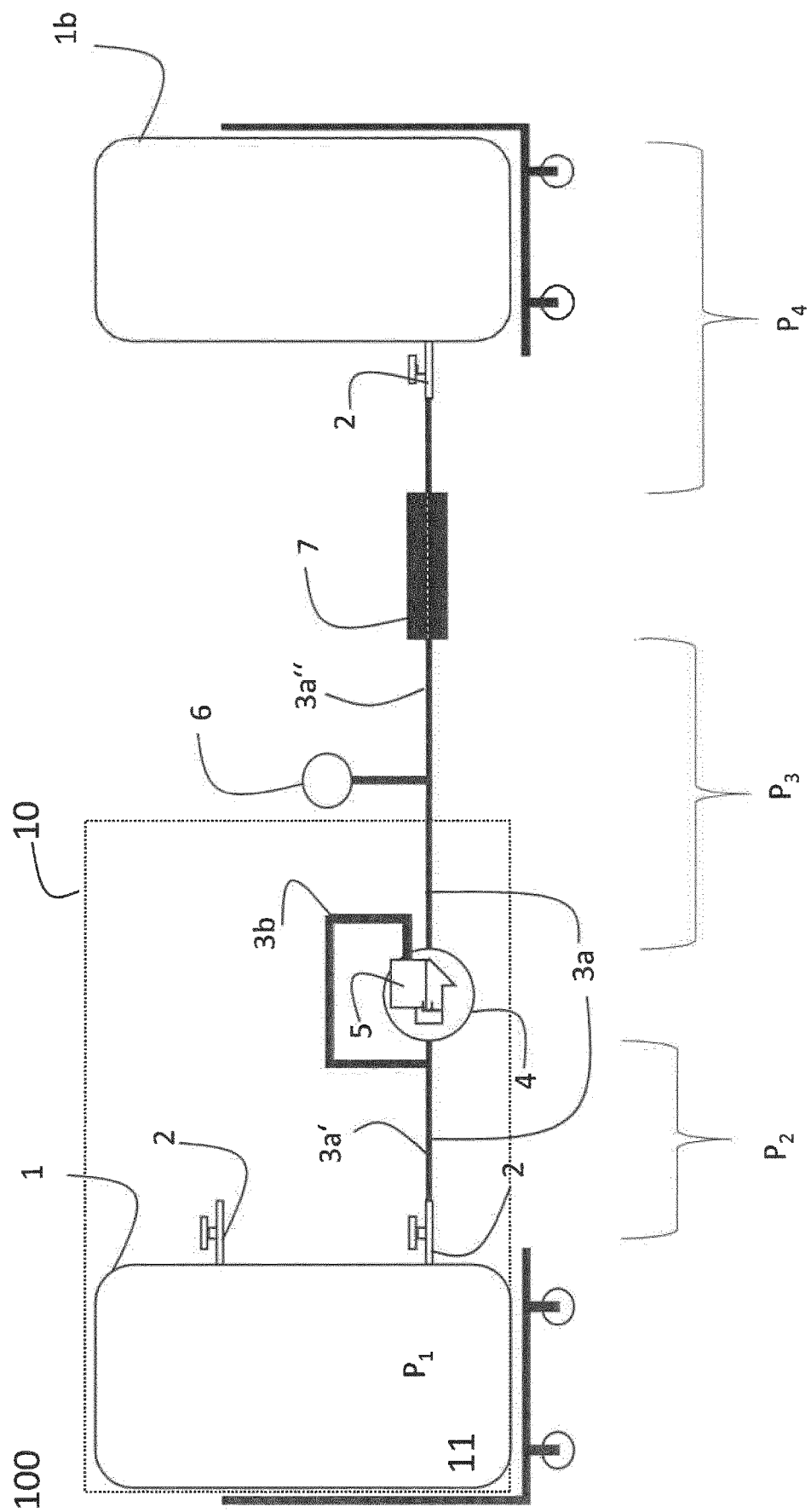
FIG. 7 is a schematic side view of a system having a device comprising a disposable container, a pump, an overpressure protection means which is integrated in the pump and a bypass line which is integrated in the pump according to an embodiment.

FIG. 7 also shows a system 100 according to another embodiment, which comprises a device 10. On a main line $3a$, there is arranged a pressure-producing means 4 which comprises an internal or integrated overpressure protection means 5. Furthermore, the system 100 comprises a bypass line $3b$. As soon as the pressure $P_3$ exceeds a specific (predetermined or predeterminable) activation pressure of the overpressure protection means 5, the overpressure protection means 5 is activated and discharges at least a portion of the at least one medium 11 into the bypass line $3b$. The bypass line $3b$ is in this instance configured to return the corresponding medium 11 into a portion $3a'$ of the system 100 which is arranged upstream of the overpressure protection means 5—with respect to the stream or flow direction F in the main line $3a$—and thus of the main line $3a$. This is possible when the pressure $P_2$ in front of the pump 4 has a lower value than the pressure $P_3$ between the pump 4 and filter 7. In this manner, the pump $P_3$ in a portion $3a''$ of the system 100 located downstream of the overpressure protection means 5—with respect to the flow direction F in the main line $3a$—and thus of the main line $3a$, can be reduced or at least limited.

The bypass line $3b$ may alternatively also be completely or at least partially integrated in the pressure-producing means 4 or in the pump 4, At least the pump 4 may have a connection for a bypass line 36.

Figure 8:
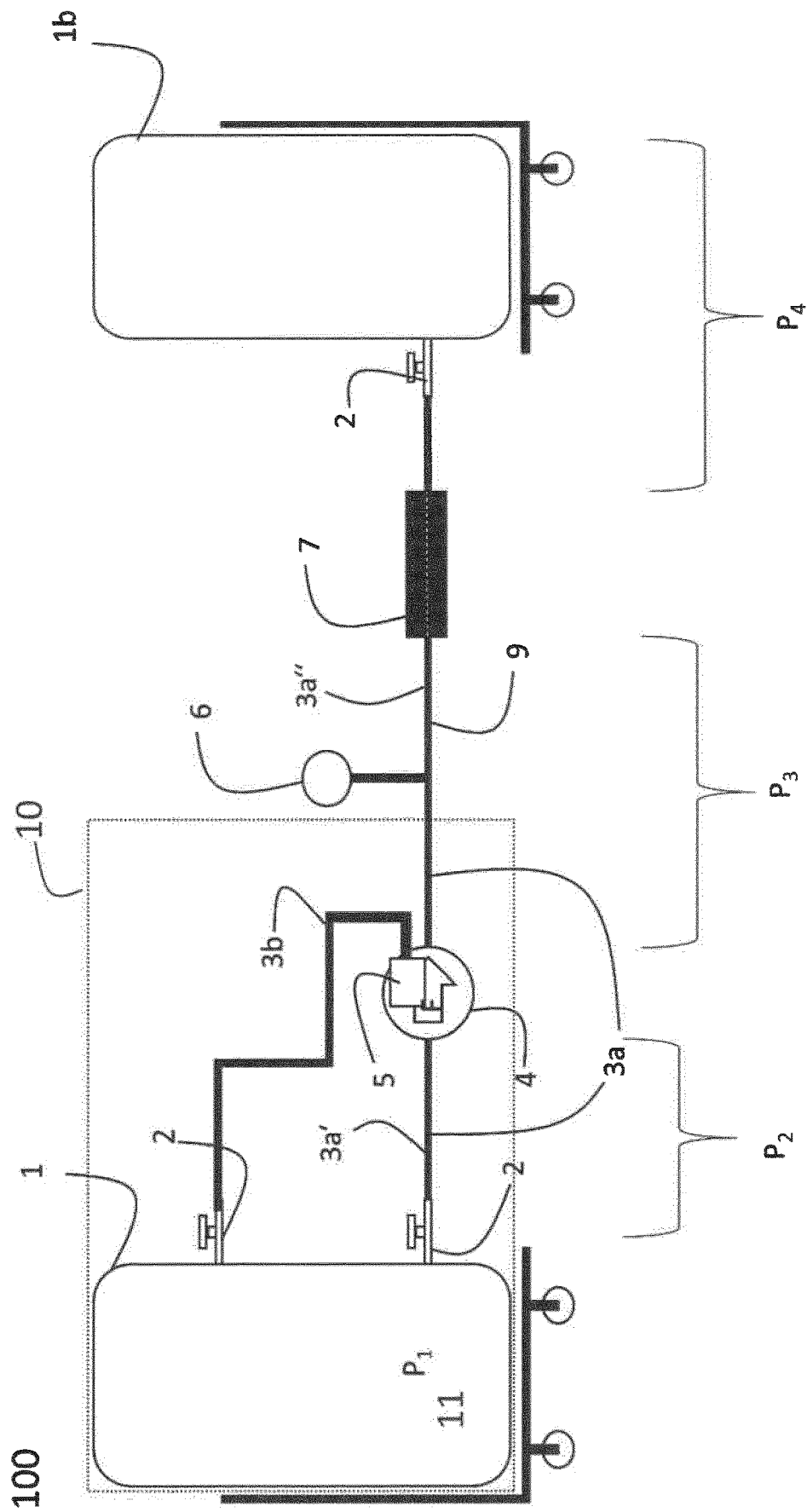
FIG. 8 is a schematic side view of a system having a device comprising a disposable container, a pump, an overpressure protection means which is integrated in the pump and a bypass line according to an embodiment.

FIG. 8 also shows a system 100 according to another embodiment which comprises a device 10. On a main line $3a$ there is arranged a pressure-producing means 4 or a pump 4 which comprise(s) an internal or integrated overpressure protection means 5. Furthermore, the system 100 also comprises a bypass line $3b$. As soon as the pressure $P_3$ has exceeded a specific (predetermined or predeterminable) activation pressure of the overpressure protection means 5, the overpressure protection means is activated and directs at least a portion of the at least one medium 11 into the bypass line $3b$. The bypass line $3b$ is in this instance configured to return the corresponding medium 11 into a portion $3a'$ of the system 100 which is located upstream of the overpressure protection means 5—with respect to the stream or flow direction F in the main line $3a$—and thus into the disposable container 1.

In this case, the bypass line $3b$ may also be at least partially integrated in the pressure-producing means 4 or in the pump 4. The pump 4 may at least have a connection for a bypass line 36.

Figure 9:
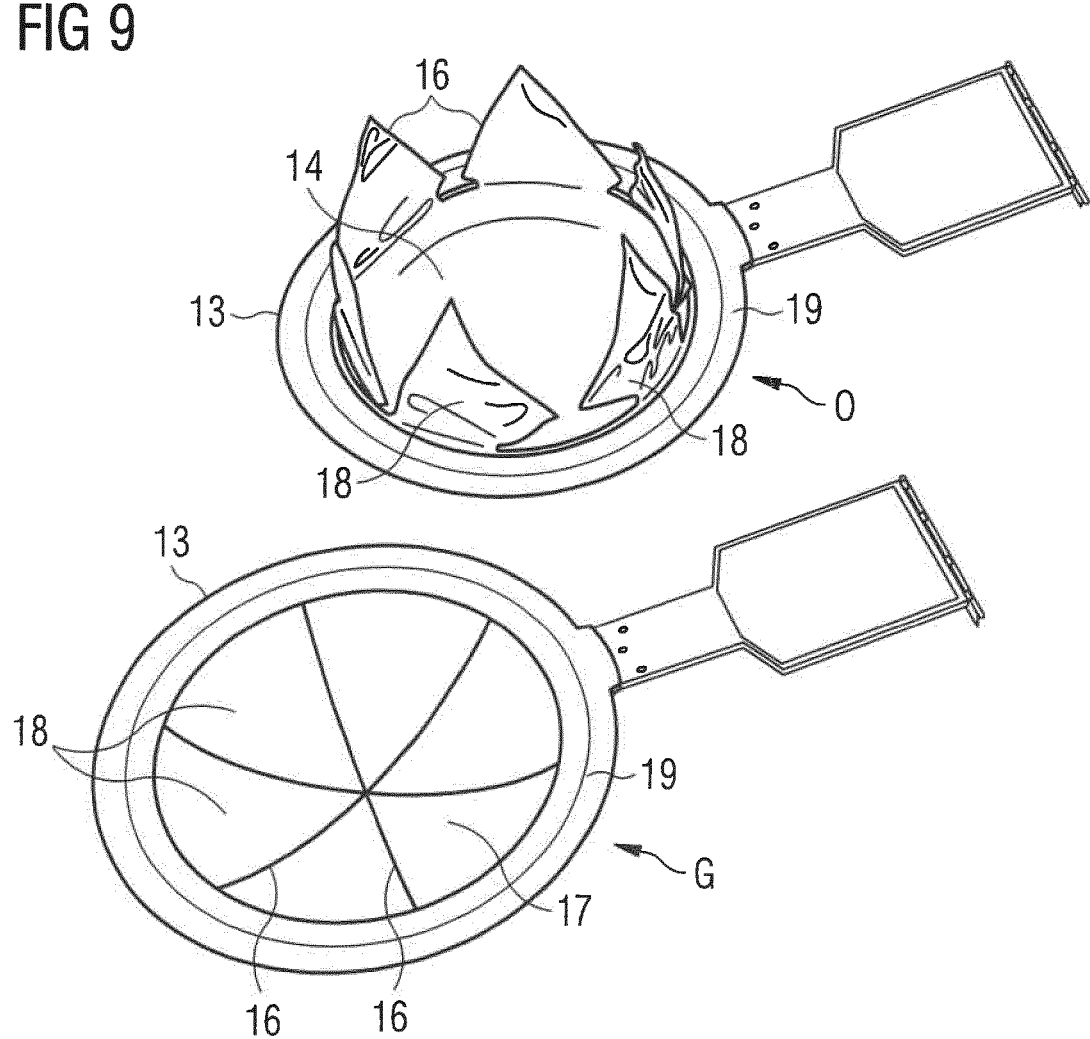
FIG. 9 shows a bursting disk in an open state after it has been activated and a bursting disk in a closed state prior to being activated according to an embodiment.

FIG. 9 shows another embodiment of an overpressure protection means 5, that is, a bursting disk 13 which is present in an intact closed state G and in a burst or activated or open state O. The overpressure protection means 5 is formed at least partially from metal, in particular an aluminum and/or high-grade steel. Alternatively, the bursting disk 13 may also be formed from a plastics material, particularly when corrosion of the material is intended to be prevented.

In the closed state G, one or more desired breaking locations 15 or seams can be seen on the closed face of the bursting disk. The convex-curved face 17 is subdivided into six triangular part-portions 18 of the convex-curved face 17 of the bursting disk 13, which are separated from each other by means of a desired breaking location 16. The desired breaking locations 16 are in this instance arranged symmetrically within an annular frame 19.

In the open state O, which corresponds to the state when the bursting disk 13 has been activated, the triangular part-portions 18 of the convex-curved face 17 of the bursting disk 13 are released or detached from each other along the desired breaking locations 16 so that they are retained only by an annular frame 19 and substantially form an opening 14.

During activation (particularly when the specific (predetermined or predeterminable) activation pressure is reached), the bursting disk 13 bursts or breaks or opens along the desired breaking locations 16 in a fragment-free manner so that no particles and/or element of the bursting disk 13 is introduced into the system 100 and/or the medium 11. Generally, a bursting disk 13 has an activation pressure. The bursting disk 13 is accordingly configured in such a manner that it bursts when this activation pressure is exceeded. This may, for example, be predetermined or defined by the selection of the material and/or the stability of the desired breaking locations 16 and/or the curvature of the bursting disk 13.

FIG. 10 shows another embodiment of an overpressure protection means 5, that is, a non-return valve 15 according to an embodiment. A non-return valve 15 or a check valve is a component which ensures the flow of a fluid in only one direction. FIG. 10 shows a resiliently loaded non-return valve 15 in which a closure element 20 is closed in one direction by means of a restoring spring 21 and in the other direction is in contrast released by the pressure of a flowing fluid. In this instance, in particular a ball is used as a closure element 20. Alternatively, a cone, a flap or a membrane can be pressed into the respective seat. If there is a pressure in the passage direction which can overcome the force of the restoring spring 21, the closure element 20 is separated or raised from its seat and the throughflow is ensured. Other embodiments also have no spring, wherein the closure element 20 can only open as a result of the flowing fluid and in particular can close as a result of the weight force of the closure element 20.

It is self-evident that the overpressure protection means 5 shown in FIGS. 9 and 10 may be integrated in one of the devices 100 and/or one of the systems 10 and/or one of the disposable containers 1 and/or containers 1a, 1b or be included thereby or connected thereto.

The above-described embodiments of the device 10, the system 100 and the method can be used in different sectors. In particular, the sector of biotechnology is involved, but other application areas may also be considered, such as, for example: food technology, drinks technology, chemical industry, chemical research, laboratory requirements, medical technology (for example, accessories for blood reserves and/or dialysis and/or infusions), process chemistry, technical chemistry.

The following process(es) can inter alia take place within a container: chemical and/or biological and/or biochemical and/or physical processes, in particular fermentation, digestion, distillation, cleaning, decomposition, aerobic processes, anaerobic processes. In particular, the device 10, system 100 and method can be used together with FlexAct systems, Sartoflow Crossflow installations, chromatography installations and installations for cell harvesting and single-use or disposable bioreactors.

The device 10 and the embodiments thereof may, for example, also be used in the storage and/or processing of hazardous and/or toxic and/or explosive chemicals. For example, a bottle in which an explosive and/or toxic substance of a medium is stored and/or transported, may comprise an overpressure protection means which is configured to direct at least a portion of the medium in the event of an overpressure into another vessel or another container. Another case could relate to a waste canister for solvents in which often hazardous and/or reactive solvent mixtures may be located. Such a waste canister or a bottle, as mentioned above, may be considered to be, for example, a disposable container and part of the device according to the invention.

This would have the advantage that uncontrolled discharge of at least one of the media mentioned and/or the substances mentioned or even bursting of the canister and/or bottle can be prevented.

In other words, a disposable element, such as a disposable container 1, in particular a disposable bioreactor, has the advantage that it can be provided in a sterile state and after use and contamination with the content does not have to be cleaned or autoclaved again, but instead can be disposed of. By using cost-effective materials to produce disposable bioreactors, processes can be carried out or implemented in a particularly cost-effective manner. All the components of a device, a system and a container, in particular a bioreactor, and all the accessories can be constructed as disposable elements. Alternatively, only individual components of a device, a system and a container, in particular of a bioreactor, may be constructed as disposable elements, whereas other components constitute reusable elements.

A medium 11 or media in the context of the present invention is/are considered to be in particular liquids, gases, suspensions, dispersions, buffers and/or cell culture broths. Media may further also include solids, such as, for example, powders, pressed pellets, particles, grains and mixtures thereof. A medium may accordingly comprise different components with the same or different aggregation states, for example, an emulsion or a dispersion.

Containers in the context of the present invention are intended to be understood in particular to be disposable containers 1. Preferably, they are disposable or single-use bags of a soft plastics material. Containers may comprise one or more of the following: containers for mixing, storing and/or transporting and bioreactors or containers as a component of bioreactors and fermenters, but also vessels, canisters and containers for storing media and/or buffer solutions. A bioreactor or fermenter may comprise or constitute a container. The container may further also be, for example, a mixing tank or container, a storage container, a bottle, a canister or a food tank or vessel. The container may also be containers in which chemical material is stored, transported and/or processed, a container may also be a chemical laboratory device, for example, a column vessel for column chromatography, a vessel or an element, for example, of a distillery. A container may in particular be at least partially formed from plastics material. Alternatively, a container may also be at least partially formed from a metal, in particular from steel. Furthermore, a container may at least partially be formed from glass. It should be expressly mentioned that the containers mentioned may also be reusable containers. For example, a collection container may also be a canister which can be configured for multiple use.

Containers, such as bioreactors, mixing systems and pellet tanks, serve substantially to receive, store and/or mix biological media, such as, for example, fluids and/or solids and/or gases. Biological media may be provided in containers, such as, for example, bags, in particular in plastics bags which may include a volume of several hundred or even several thousand liters. The biological media may preferably be introduced inside such a bag into the bioreactor in which they can be stored, temperature-controlled and/or mixed.

Disposable containers 1 may in particular be integrated in filtration/fermentation and reconditioning installations, such as, for example, virus filtration/chromatography or cross-flow installations.

The disposable container 1 may be a disposable bioreactor bag having flexible walls, such as, for example, a Biostat® Cultibag® agitation reactor, bioreactor bag, a Cultibag® RM-Rocking bioreactor bag of the Wave® type, an agitation bag of the Agitation-ORB® type or other flexible bioreactor bags. The disposable container 1 may further be a disposable 3D bioprocess bag, for example, a Palletank® storage or mixing bag, a LevMix® or MagMix® mixing bag, other flexible 3D bioprocess bags or 3D bag covers. The disposable container 1 may also be a disposable bioprocess bag with 2 dimensions, for example, a FlexBoy®, Celsius® or other 2D-bioprocess bag. The disposable container 1 may also be a disposable bioreactor container with rigid container walls 12, such as, for example, the Biostat® SU, the TAP Biosystems ambr15, the ambr250 and other rigidly covered bioreactor containers. The disposable container 1 may also be a rigid-walled CellSTACK® container for single use which is a multi-chamber plastics material container with rigid walls. For example, for tissue culture of growing adherent cells inter alia fixed wall CellSTACK® containers are used.

The term "activating an overpressure protection means 5" is in particular intended to be understood to mean that the overpressure protection means 5 performs its function at the time at which it is activated. In particular, an activation may involve a pressure exceeding a maximum value and thus an activation pressure, whereby an overpressure protection means 5 is activated in such a manner that it forms an opening and consequently can at least prevent the pressure P within the device 10 or a portion of the device 10 from rising further. Through the opening, after the activation of the overpressure protection means 5, at least a portion of the medium 11 located in the device 10 can escape and/or be discharged in a controlled manner and/or be discharged and/or returned. In specific cases, after an overpressure protection means 5 has been activated, the pressure P in the device 10 or in at least a portion of the device may even be reduced compared with the value prior to the activation.

An overpressure protection means 5 may also be connected in fluid terms to at least one filter. Such a filter may, without being limited thereto, be or comprise a hydrophobic ventilation filter, a hydrophilic liquid filter, a sterilizing filter, a virus retention filter, a combined hydrophilic/hydrophobic filter, a blocking filter, a filter series with a plurality of filters. Filters may prevent toxic and/or hazardous substances, in particular aerosols which are discharged from the system 100 and/or the device 10, from impairing a user and/or escaping into the environment.

A line 3, a bypass line 3b, a discharge 3c and/or an overpressure protection means 5 may comprise at least one filter, in particular a membrane filter. The filter may, without being limited thereto, be a hydrophobic ventilation filter, a hydrophilic liquid filter, a sterilizing filter, a virus retention filter, a combined hydrophilic/hydrophobic filter, a blocking filter and/or a filter line with a plurality of filters. A branch or a combination of filters may also be provided and can include separate hydrophilic and hydrophobic filters.

A device 10 comprises at least the features of the device 10 which are included by the first main claim. The embodiments of the device 10 illustrated by way of example in the drawings or Figures also include additional features which are intended to be understood to be optional.

A target container comprises all known containers which are considered to be disposable containers. Furthermore, a target container comprises an open or closed vessel, a (pipe) line, a container, a (bio) reactor and other containers for preparing or processing fluids.

LIST OF REFERENCE NUMERALS

1 Disposable container
1a Additional second container
1b Additional third container also called target container
2 Inlet and/or outlet
3 Line
3a Main line
3a' Portion arranged upstream of the overpressure protection means with respect to a flow direction in the main line
3a" Portion arranged downstream of the overpressure protection means with respect to a flow direction in the main line
3b Bypass line
3c Discharge
4 Pressure-producing means, for example, a pump
5 Overpressure protection means
6 Pressure measuring device, for example, manometer
7 Resistance, for example, filter (installation)
8 Feedback between the overpressure protection means and pump
9 System which may be open or closed
10 Device
10a First part-system which is closed or open
10b Second part-system which is closed or open
11 Medium
12 Container walls
13 Bursting disk
14 Opening in the bursting disk
15 Non-return valve
16 Desired breaking locations or seam
17 Convex-curved face of a bursting disk
18 Triangular part-portions of the convex-curved face of a bursting disk
19 Annular frame
20 Closure element of a non-return valve
21 Restoring spring of a non-return valve
100 System
F Flow direction
G Closed state of the overpressure protection means
O Open state of the overpressure protection means
P Pressure in front of the overpressure protection means
$P_1$ Pressure in the container
$P_2$ Pressure in the main line in front of the pump
$P_3$ Pressure in the main line after the pump
$P_4$ Pressure in the main line and where applicable in the second container after the resistance
$P_5$ Pressure in front of the pressurized disposable container
$P_6$ Pressure in the discharge and where applicable in the third container
V Container volume of the disposable container
ZV Target volume

The invention claimed is:
1. A system comprising:
a bioprocess device comprising:
at least one disposable container which is configured to at least partially receive at least one medium; and
at least one overpressure protection means which is connected to the at least one disposable container in fluid terms, wherein the at least one overpressure protection means is configured, in the event of an activation, to guide the at least one medium at least partially into a device region which is arranged upstream of the overpressure protection means with respect to a flow direction, and/or into the at least one disposable container; and/or into at least one additional second container;

a main line for fluid connection of the at least one disposable container to a target container; and at least one of:

at least one discharge which is configured, when the at least one overpressure protection means is activated, to direct the at least one medium at least partially into at least one additional container; or a bypass line which is configured, when the at least one overpressure protection means is activated, to direct the at least one medium at least partially back into the device region which is arranged upstream of the overpressure protection means with respect to a flow direction, including into a portion of the main line and/or into the at least one disposable container, wherein the at least one overpressure protection means is arranged on the discharge and/or the bypass line and, when the at least one overpressure protection means is activated, the discharge and/or the bypass line is/are connected in fluid terms to the main line; and at least one pressure-producing means, including a pump, wherein the at least one pressure-producing means is configured to pump at least a portion of the at least one medium from the at least one disposable container into the third container in the flow direction, wherein the at least one pressure-producing means is arranged in fluid communication with the disposable container and is configured to produce a pressure drop within the disposable container and/or along the main line.

2. The system of claim 1, wherein the at least one overpressure protection means is integrated directly in container walls of the at least one disposable container.

3. The system of claim 1, wherein the at least one overpressure protection means comprises a disposable overpressure protection means, including a mechanical overpressure protection means, which is at least partially formed from a high-grade steel and/or a plastics material.

4. The system of claim 1, wherein the at least one overpressure protection means comprises at least one of the following: a bursting disk, an overflow valve, a safety valve, a membrane, or an electrical and/or mechanical force limiter of a pump.

5. The system of claim 1, further comprising at least one discharge which is configured, when the at least one overpressure protection means is activated, to direct the at least one medium at least partially into the at least one disposable container and/or into the at least one second container.

6. System as claimed in claim 1, further comprising the target container which is configured to at least partially receive the at least one medium and which is a disposable container.

7. The system as claimed in claim 1, wherein the at least one pressure-producing means is arranged on the main line and is configured to produce a pressure drop along the main line.

8. The system as claimed in claim 1, wherein the discharge and/or the bypass line is/are integrated at least partially in the pressure-producing means.

9. The system as claimed in claim 1, further comprising a feedback, including an electrical feedback, between the overpressure protection means and pressure-producing means, wherein the feedback is configured to switch off the pressure-producing means when the at least one overpressure protection means is activated.

* * * * *